US010820960B2

(12) United States Patent
Manley

(10) Patent No.: US 10,820,960 B2
(45) Date of Patent: Nov. 3, 2020

(54) CANNULA LOCK WITH A BRAKE THAT ROTATES AND ANCHORS THAT DEPLOY INTO THE BONE AGAINST WHICH THE CANNULA LOCK IS SET

(71) Applicant: Stryker European Holdings I, LLC, Kalamazoo, MI (US)

(72) Inventor: Kevin Manley, Cobh (IE)

(73) Assignee: Stryker European Holdings I, LLC, Kalamazoo, MI (US)

( * ) Notice: Subject to any disclaimer, the term of this patent is extended or adjusted under 35 U.S.C. 154(b) by 199 days.

(21) Appl. No.: 16/093,677

(22) PCT Filed: Apr. 14, 2017

(86) PCT No.: PCT/US2017/027546
§ 371 (c)(1),
(2) Date: Oct. 15, 2018

(87) PCT Pub. No.: WO2017/180950
PCT Pub. Date: Oct. 19, 2017

(65) Prior Publication Data
US 2019/0133708 A1      May 9, 2019

Related U.S. Application Data
(60) Provisional application No. 62/322,915, filed on Apr. 15, 2016.

(51) Int. Cl.
*A61B 90/11*      (2016.01)
*F16C 11/06*      (2006.01)
(Continued)

(52) U.S. Cl.
CPC .......... *A61B 90/11* (2016.02); *F16C 11/0609* (2013.01); *F16C 11/106* (2013.01); *A61B 2090/103* (2016.02); *F16C 2316/10* (2013.01)

(58) Field of Classification Search
None
See application file for complete search history.

(56) References Cited

U.S. PATENT DOCUMENTS
2,928,686 A    3/1960   Newkirk
3,240,516 A    3/1966   Barish et al.
(Continued)

FOREIGN PATENT DOCUMENTS
DE    707617 C    6/1941
DE    19904061 A1    7/1999
(Continued)

OTHER PUBLICATIONS
Machine-assisted English translation for DE 707 617 extracted from espacenet.com database on Nov. 7, 2018, 8 pages.
(Continued)

*Primary Examiner* — Shaun L David
(74) *Attorney, Agent, or Firm* — Howard & Howard Attorneys PLLC

(57) ABSTRACT

A cannula lock for holding a medical device static in a select orientation relative to tissue. The cannula lock includes a shell with anchors. The anchors are deployed to the hold the shell static to the tissue. A pivoting brake (95) is disposed in the shell. The brake holds the medical device. When the orientation of the brake, by extension, the orientation of the device is established, the brake is set. The brake is set by expanding the brake (95) outwardly against the inner surfaces of the shell so as to hold the brake and medical device in the select orientation.

20 Claims, 18 Drawing Sheets

(51) Int. Cl.
*F16C 11/10* (2006.01)
*A61B 90/10* (2016.01)

(56) References Cited

U.S. PATENT DOCUMENTS

| | | | | |
|---|---|---|---|---|
| 5,263,956 | A * | 11/1993 | Nobles | A61B 90/11 606/1 |
| 5,658,272 | A | 8/1997 | Hasson | |
| 5,993,463 | A * | 11/1999 | Truwit | A61B 90/11 606/129 |
| 6,267,769 | B1 * | 7/2001 | Truwit | A61B 90/11 606/1 |
| 6,328,748 | B1 * | 12/2001 | Hennig | A61B 17/3403 606/130 |
| 6,432,058 | B1 | 8/2002 | Sloth | |
| 6,716,215 | B1 | 4/2004 | David et al. | |
| 6,752,812 | B1 * | 6/2004 | Truwit | A61B 90/11 606/1 |
| 7,824,417 | B2 * | 11/2010 | Magnusson | A61B 17/3403 606/130 |
| 8,165,658 | B2 | 4/2012 | Waynik et al. | |
| 8,747,419 | B2 * | 6/2014 | Solar | A61B 90/11 606/130 |
| 2002/0049451 | A1 * | 4/2002 | Parmer | A61B 90/11 606/108 |
| 2003/0040753 | A1 | 2/2003 | Daum et al. | |
| 2004/0243146 | A1 * | 12/2004 | Chesbrough | A61B 90/11 606/130 |
| 2004/0260312 | A1 * | 12/2004 | Magnusson | A61B 17/3403 606/130 |
| 2006/0089626 | A1 * | 4/2006 | Vlegele | A61B 34/20 606/1 |
| 2008/0183191 | A1 * | 7/2008 | Schoepp | A61B 17/3403 606/130 |
| 2008/0200798 | A1 * | 8/2008 | Eklund | A61B 90/11 600/414 |
| 2010/0042111 | A1 * | 2/2010 | Qureshi | F16M 11/36 606/130 |
| 2013/0072876 | A1 * | 3/2013 | Pretre | A61M 25/04 604/175 |
| 2013/0096570 | A1 * | 4/2013 | Solar | A61B 90/11 606/108 |
| 2013/0158578 | A1 * | 6/2013 | Ghodke | A61B 17/320783 606/170 |
| 2014/0018822 | A1 * | 1/2014 | Main | A61B 17/3403 606/130 |
| 2014/0378997 | A1 * | 12/2014 | Ross | A61B 90/11 606/130 |
| 2015/0119753 | A1 * | 4/2015 | Cosgrove | A61B 5/4064 600/562 |
| 2015/0127040 | A1 | 5/2015 | Gill et al. | |
| 2015/0265216 | A1 * | 9/2015 | Andrews | A61B 6/0492 128/845 |
| 2016/0074063 | A1 * | 3/2016 | Arimitsu | A61B 10/0233 606/130 |
| 2016/0166355 | A1 * | 6/2016 | Farah | A61B 90/39 606/130 |
| 2016/0367332 | A1 * | 12/2016 | Shah | A61B 90/11 |
| 2017/0007349 | A1 * | 1/2017 | Solar | A61B 17/00234 |
| 2017/0151032 | A1 * | 6/2017 | Loisel | A61B 90/11 |
| 2017/0296289 | A1 * | 10/2017 | Andrews | A61B 34/30 |

FOREIGN PATENT DOCUMENTS

| | | |
|---|---|---|
| EP | 2653130 A1 | 10/2013 |
| WO | 2016178857 A1 | 11/2016 |

OTHER PUBLICATIONS

English language abstract and machine-assisted English translation for DE 199 04 061 extracted from espacenet.com database on Nov. 7, 2018, 6 pages.

International Search Report for Application No. PCT/US2017/027546 dated Sep. 1, 2017, 5 pages.

* cited by examiner

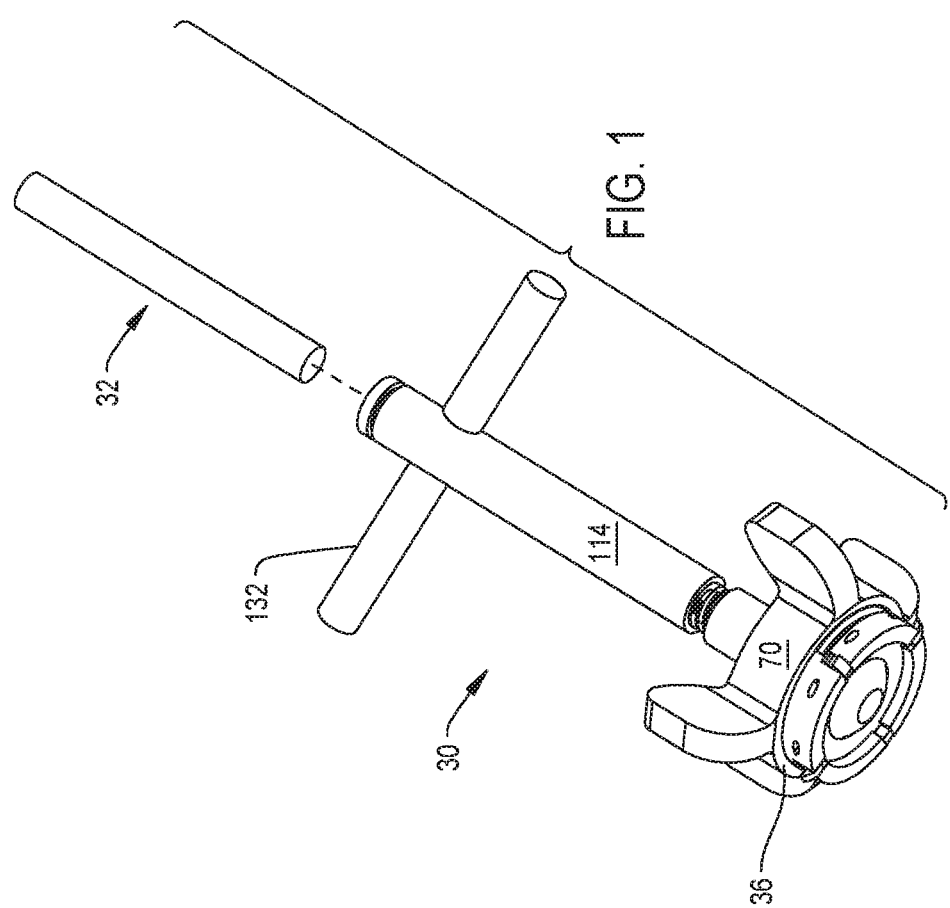

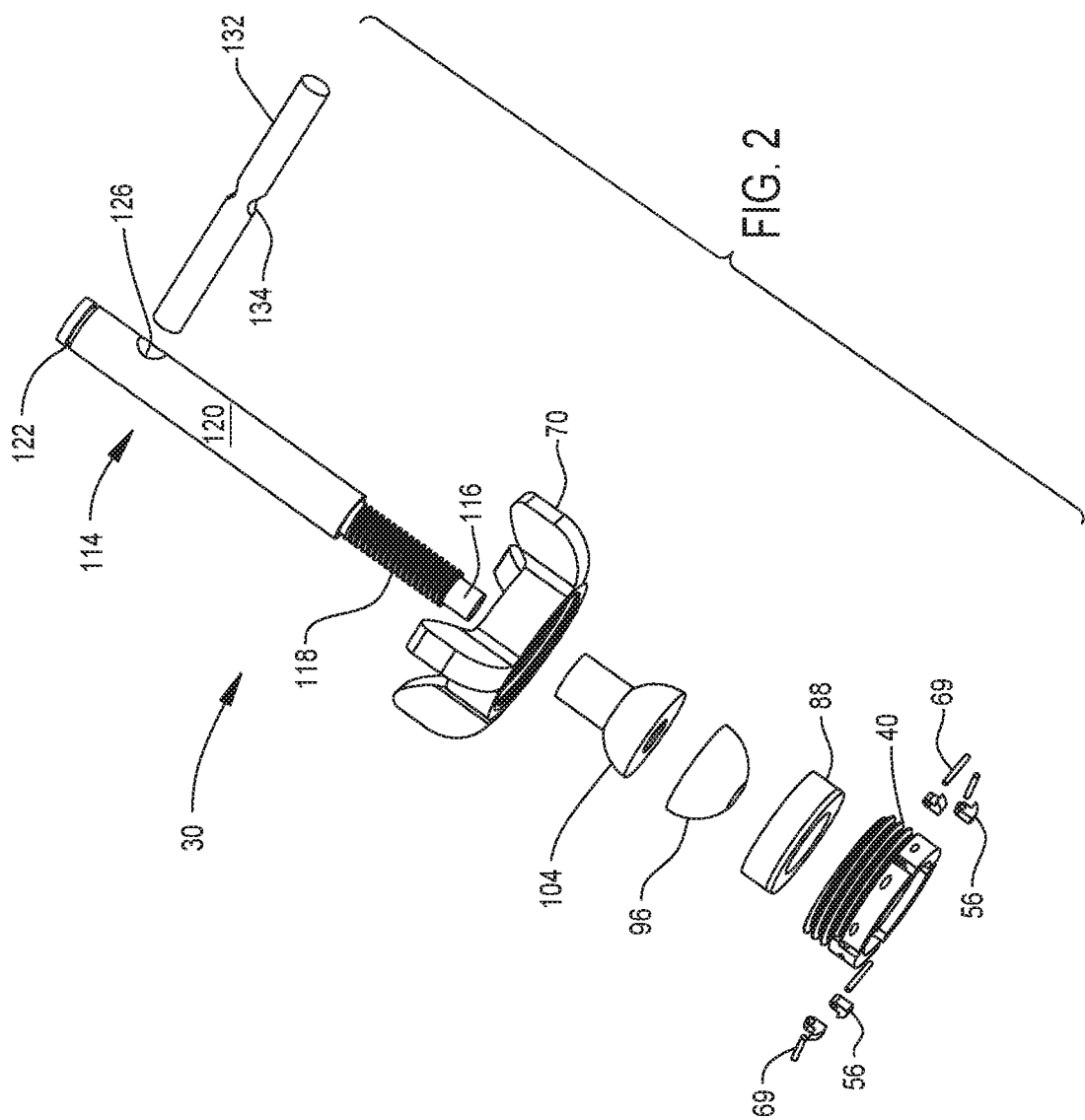

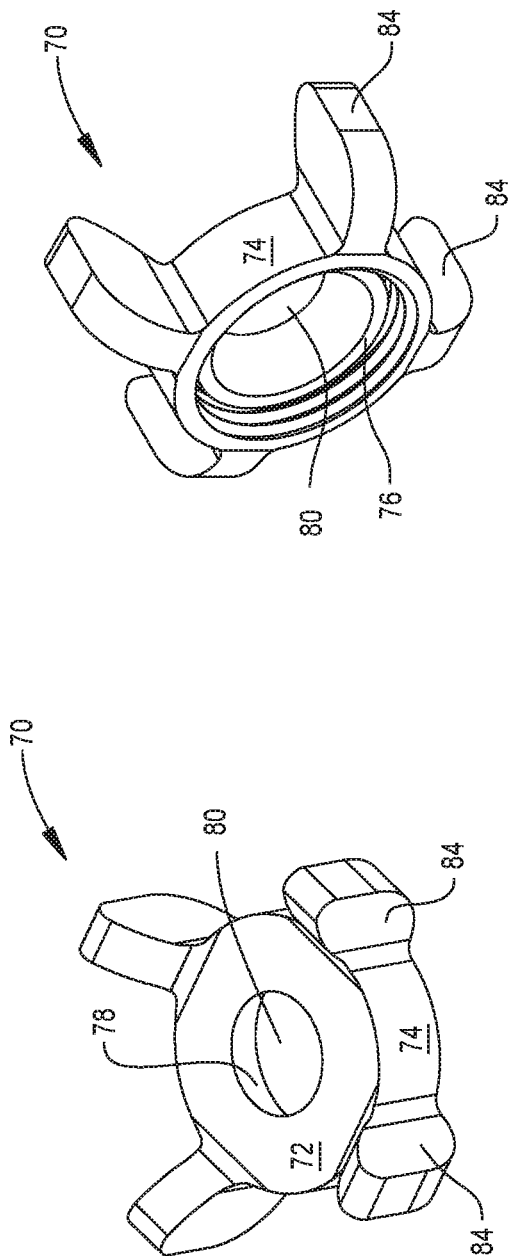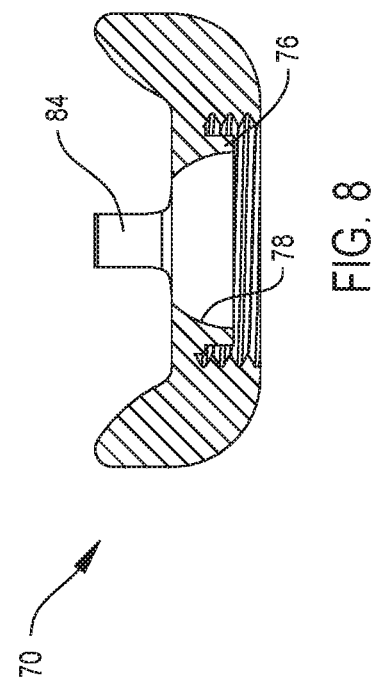

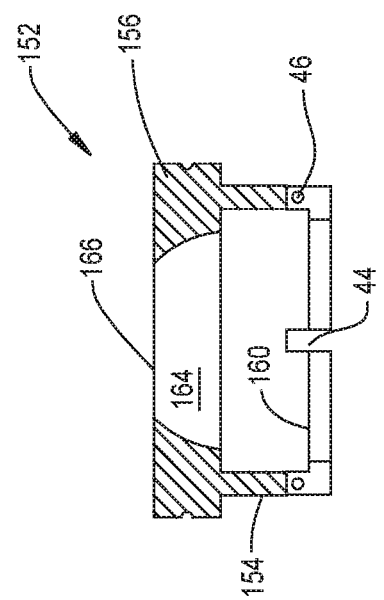
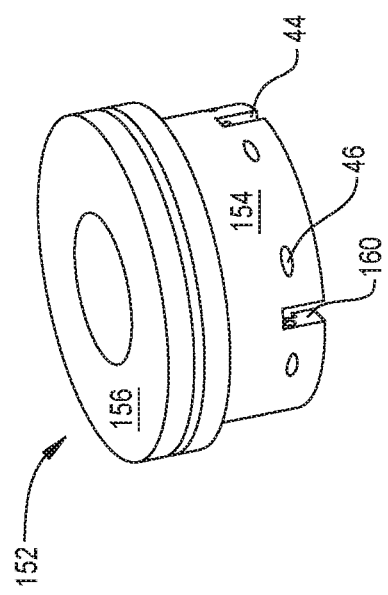

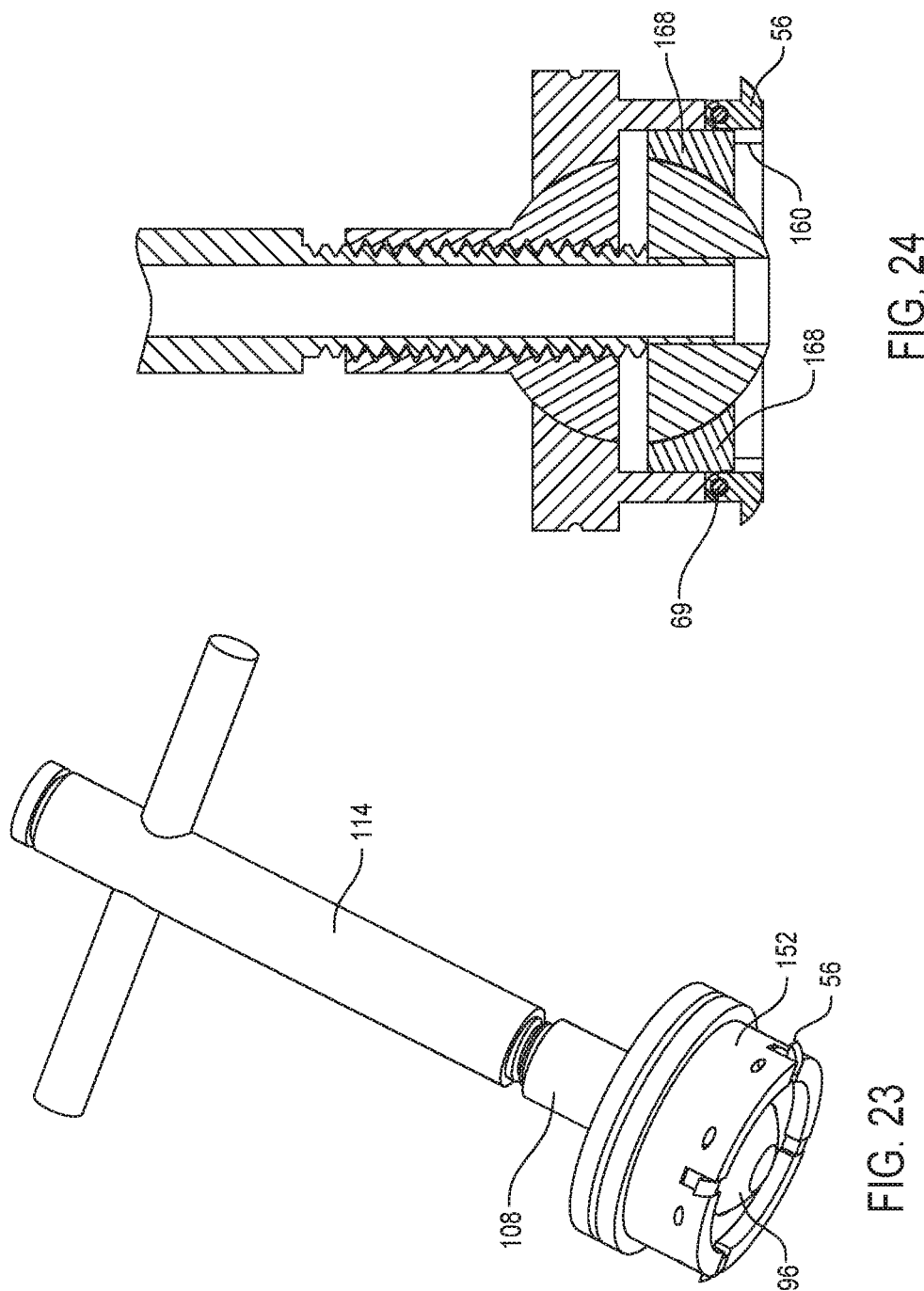

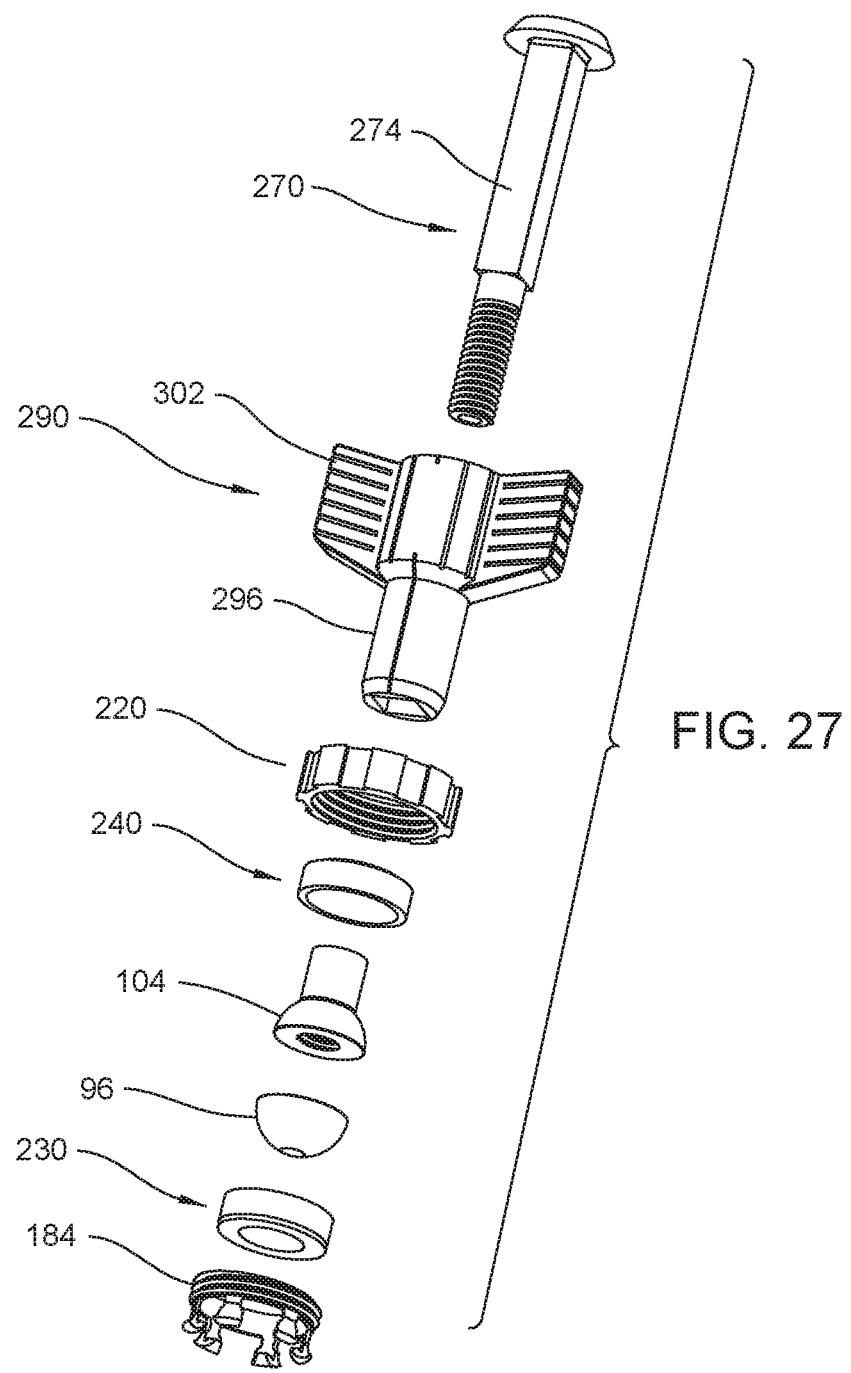

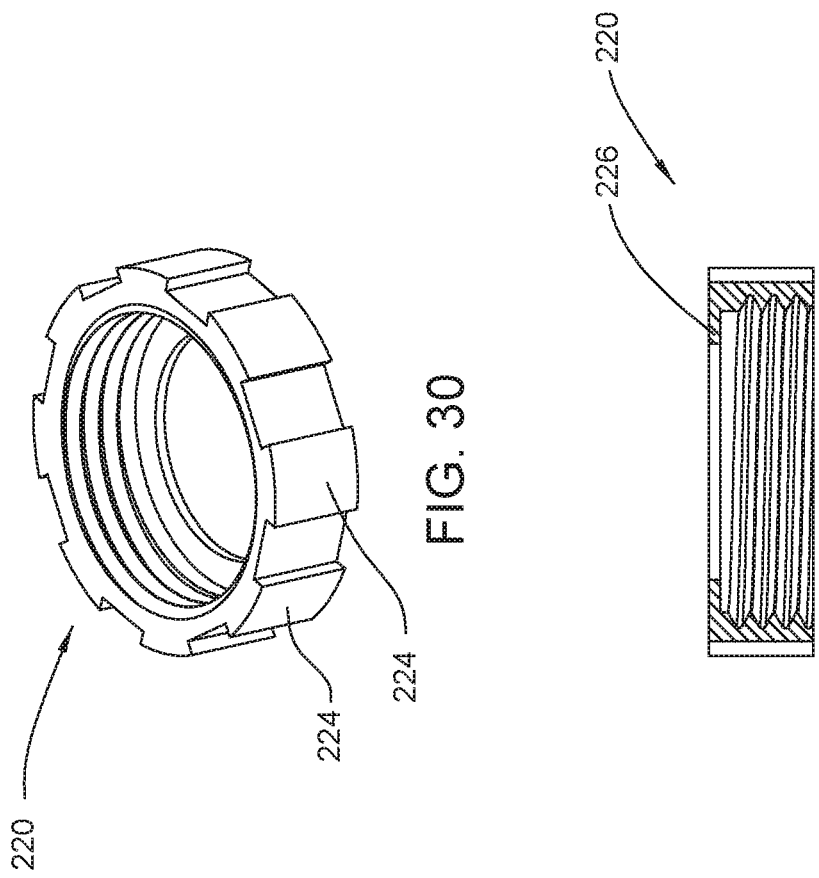

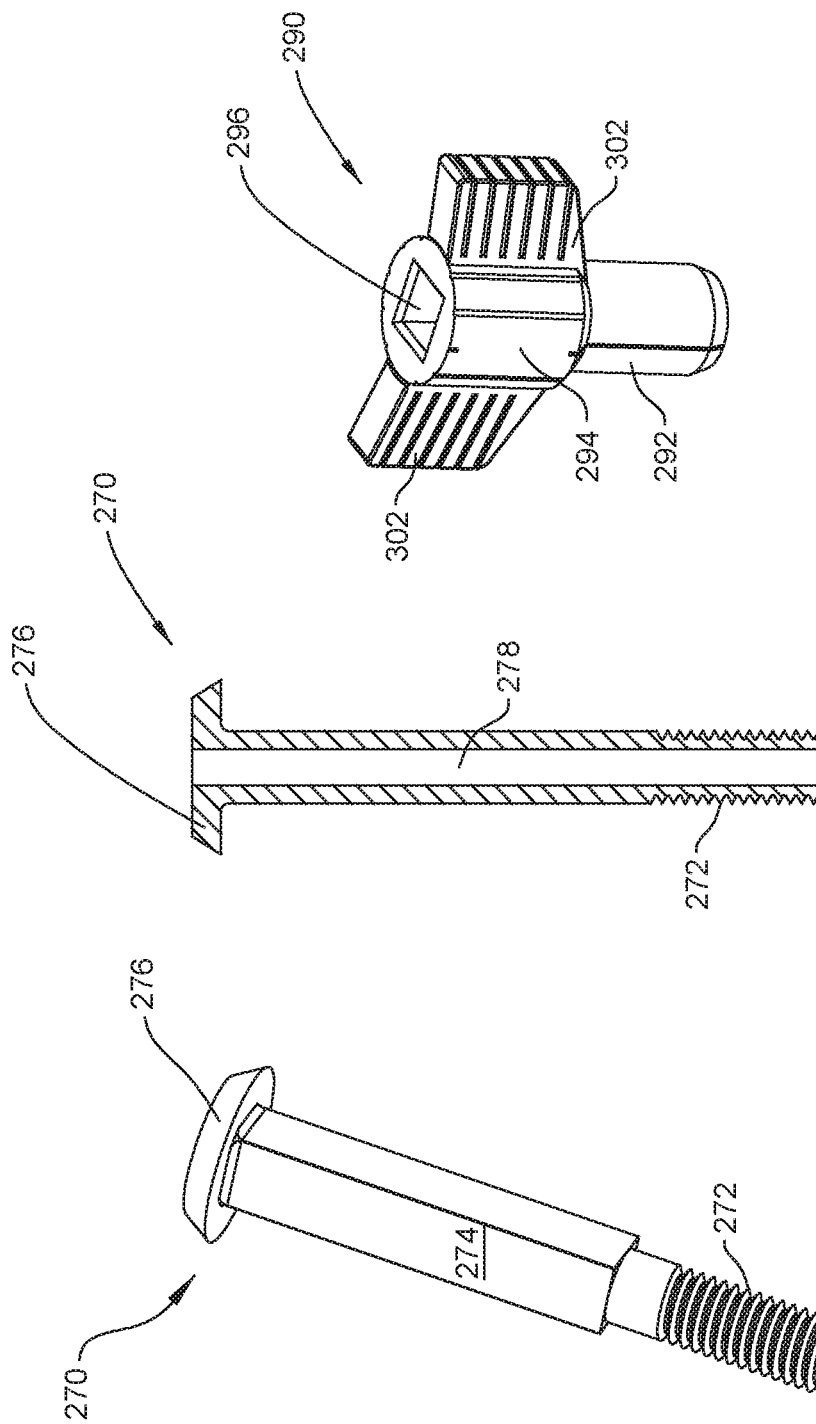

CANNULA LOCK WITH A BRAKE THAT ROTATES AND ANCHORS THAT DEPLOY INTO THE BONE AGAINST WHICH THE CANNULA LOCK IS SET

This application is a U.S. National Stage of International Patent Application No. PCT/US2017/027546, filed on Apr. 14, 2017, which claims the benefit of and priority to U.S. Provisional Patent Application Ser. No. 62/322,915, filed on Apr. 15, 2016, the entire contents of each are hereby incorporated by reference in their entireties.

FIELD OF THE INVENTION

This invention relates generally to a cannula lock used to hold a cannula or other device to a patient. The cannula lock of this invention includes anchors and an assembly for setting the anchors to secure the cannula lock in place to the section of the tissue against which the cannula lock is seated. The cannula lock of this invention is further configured to facilitate the locking of the device in a fixed angular orientation independent of the orientation of the device.

BACKGROUND OF THE INVENTION

There are a number of medical and surgical procedures during which an elongated device is inserted in a portal formed in the patient. The device is inserted into the patient so that the distal end of the device is positioned at a specific target location inside an organ or a section of tissue internal to the patient. For example, when an abnormality in the brain is suspected, it is desirable to obtain a sample of tissue from the section of the brain in which this abnormality is believed to be located. To perform this procedure, a needle is precisely positioned at the targeted section of the brain. The needle is used to extract a section of the tissue so the pathology of the tissue can be analyzed to determine whether or not the abnormality is present. Once the needle is so positioned, it is necessary to hold the needle on target. The locking of the needle is necessary to both ensure that the tissue that is extracted is the desired tissue and to minimize the complications associated with performing the procedure.

A cannula lock, as implied by its name, is a device that holds a cannula, a needle or other device static when the device is inserted into a patient. Generally a cannula lock includes a base and a clamp. The base is a static structure. Components integral with or attached to the base hold the base static to a section of tissue above the target location at which the cannula or needle is to be positioned. The base includes a void. The clamp is seated in the void. The clamp is the sub-assembly of the lock that, when engaged, holds the cannula or other device static to the base. Many clamps have a shape that can generally be described as spherical. As part of the process of positioning the cannula or other device, the base is initially secured to the section of tissue above the target location. The clamp is seated in the void internal to the base. The cannula or other device is seated in a bore that extends through the clamp. The clamp is rotated. This rotation is to ensure that the cannula or other device, as the device is inserted through the lock into tissue, is on a trajectory that ensures that the distal end of the device will be positioned at the target location. Given that the clamp is typically spherical, it is usually possible to rotate the clamp around two axes that extend through the clamp. Once the cannula or other device is positioned at the target location, locking components with the lock are set. The setting of these components locks the clamp into a specific orientation relative to the base. The setting of these locking components ensures that the device remains at the intended orientation throughout the time it takes to perform the procedure.

Many cannula locks, including cannula locks used to holding a brain biopsy needle in place, do a reasonable job of fixedly holding the associated cannula or needle in place. Nevertheless, some effort may be required to use these locks. For example, a cannula lock used to hold a brain biopsy needle in place is typically held static against the skull by one or more screws. The screws extend outwardly from the base. The screws extend into sections of the skull that surround the bore formed in the skull through which the biopsy needle is inserted. A disadvantage of having to screw secure cannula lock to the patient is that the time spent screwing the screws into the patient, and then, after the needle is withdrawn, unscrewing the screws, adds to the overall time it takes to perform the procedure. This runs contrary to one of the objectives of modern surgical practice. Specifically, it is a goal to perform a procedure as quickly as possible. Performing a procedure quickly both lessens the exposure of the patient to anesthesia and minimizes the time the patient's normally covered internal tissue is exposed to the ambient environment and the infection-inducing agents inherently in this environment.

Furthermore, to have to form bores in the skull for receiving the screws adds to the trauma to which the patient's body is exposed.

Still another disadvantage of some cannula locks concerns the arrangement of their clamps. In particular, once the device being locked in place is positioned, it is necessary to manipulate some component of the clamp to place the clamp in the locked state in which the clamp rigidly holds the cannula or other device to the base. The device typically extends proximally away from the cannula lock. A problem can arise because sometimes, when the device is in specific orientation relative to the base, the device obstructs access to the manipulated component of the clamp. This can sometimes make it essentially impossible to set the clamp in the locked state. If this event occurs, it may be necessary to reposition the cannula lock. Having to so perform this task, at a minimum, adds to the overall time required to perform the procedure. In some situations if a new access bore and screw bores need to be formed, this repositioning of the cannula lock can further add to the trauma to which patient is exposed.

The cannula lock of WO 2016/178857 A1 attempts to remedy this problem. This cannula lock includes an inner ring from which a number of legs extend distally forward. The legs are bendably mounted to the ring. An inner sheath able to pivot in two axes is disposed in the ring. An elongated tube extends from the inner sheath. When it is time to set the position of the instrument set in the tube, an upper ring is rotated. As a result of the rotation of the upper ring, the inner sheath is clamped between the two rings. The inner sheath is also displaced so as to cause the outward flexure of the legs. The legs are then supposed to grab below the inner surface of the bone in which the cannula lock is seated so the lock is compressed between the outer and inner surfaces of the bone.

One concern regarding this type of device is that the practitioner requires two hands to lock the tube, in the desired position; a first hand is required to hold the tube in the desired position while the second hand is used to rotate the upper ring so as to clamp the sheath between the rings. Further, this lock requires the legs to be positioned below the bone, the skull, to anchor the lock to the bone. This requires the exact position of the lock so the legs extend below the bone of the skull but not penetrate the dura, the protective covering over the brain.

SUMMARY OF THE INVENTION

This invention is related to a new and useful cannula lock. The cannula lock of this invention holds medical devices such as cannulae and needles in a fixed position relative to the portion of the anatomy to which the lock is attached. The cannula lock of this invention includes features that hold the cannula lock to the tissue against which the cannula lock is placed that do not require the driving of screws into the tissue. The cannula lock of this assembly is further configured so that, independent of the orientation of the cannula or needle relative to the lock, the actuated component of the cannula lock that is set to hold the device in a fixed angular orientation is accessible.

The cannula lock of this invention includes a shell and a brake. The brake is disposed in the shell. Typically, at least one of the shell or brake is assembled from plural components.

The shell includes at least one anchor that is moveably attached to the rest of the shell. A drive member is disposed in the shell. The drive member is configured to, when actuated, displace the anchor from a retracted state to an extended state. When the anchor moves into the extended state, the anchor projects into tissue adjacent the shell to secure the cannula lock to the tissue. One type of tissue to which the anchor can project into is bone.

In some versions of the invention, the drive member is ring shaped. The drive member is actuated by moving a cap, which is part of the shell, against a base. The base is another component of the shell.

The brake assembly includes a base and a head, both of which are disposed in the shell. A tube connects the base and head and extends proximally away from the shell. The tube is formed with a bore that receives the cannula or other device the lock is intended to hold in place. The base and head of the brake assembly are able to rotate around at least one axis inside the shell. The brake assembly includes an actuator that selectively urge the brake base and head away from each other and against surfaces of the shell. This pressing of the brake components against the shell holds the tube and, by extension, the device in the tube, in a fixed angular orientation relative to the shell.

In some versions of the invention, the tube functions as the actuator that causes the relative movement of the head or base away from the other one of the base or head. This means that with a single hand, the person using this cannula lock can both position the tube in the desired position and, once the tube is position, lock the tube in that position.

In some versions of the invention, the base and the head of the brake collectively have an outer shape that is curved around two axes. This allows the angular orientation of the brake relative to the shell to be set around two axes that are static through the shell. In some versions of these versions of the invention, the base and head of the brake collectively have an outer shape that is spherical.

BRIEF DESCRIPTION OF THE DRAWINGS

The invention is pointed out with particularity in the claims. The above and further features and benefits of this invention are understood from the following Detailed Description taken in conjunction with the accompanying drawings in which:

FIG. 1 is a perspective view of a cannula lock of this invention;

FIG. 2 is an exploded view of the cannula lock;

FIG. 6 is a perspective view of the top of the cap of the shell;

FIG. 7 is a perspective view of the bottom of the cap of FIG. 6;

FIG. 8 is a cross sectional view of the cap of FIG. 6;

FIG. 21 is a perspective view of the shell of the alternative cannula lock;

FIG. 22 is a cross sectional view of the shell of FIG. 20;

FIG. 23 is a perspective view of the alternative cannula lock when the brake is in the set state and the anchors are in the extended state;

FIG. 24 is a cross sectional view of the alternative cannula lock when the brake is in the set state and the anchors are in the extended state;

FIG. 27 is an exploded view of the cannula lock of FIG. 25;

FIG. 30 is a perspective view of the cap of the cannula lock of FIG. 25;

FIG. 31 is a cross sectional view of the cap of FIG. 30;

FIG. 36 is a perspective view of the trunk of the cannula lock of FIG. 25;

FIG. 37 is a cross sectional view of the trunk of FIG. 36; and

FIG. 38 is a perspective view of the finger grip disposed over the trunk of FIG. 36.

DETAILED DESCRIPTION

I. First Embodiment

Figure 3:
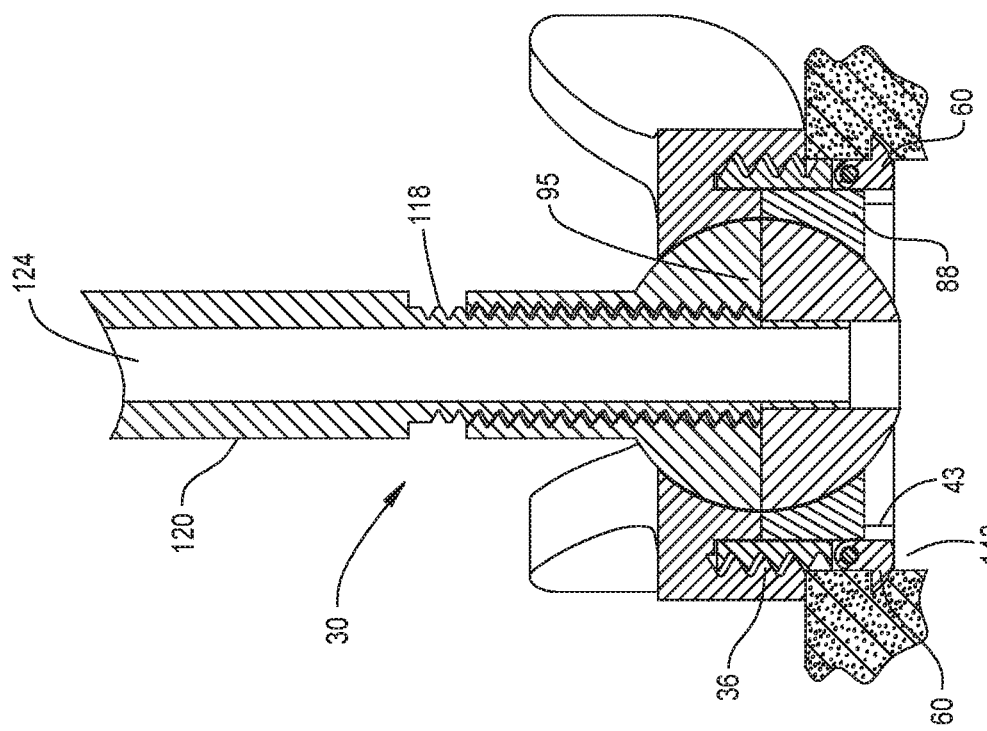
FIG. 3 is a cross sectional view of the cannula lock seated in a section of bone.

FIGS. 1, 2 and 3 depict a lock 30 of this invention. Lock 30 holds a medical or surgical device in a fixed angular orientation relative to the section of the anatomy of the patient to which the lock is attached. The depicted device, seen in FIG. 1, is a needle 32. Often the device is a cannula. A cannula, like a needle, is a tube like device. Often, cannulas are larger in diameter than needles. Accordingly, this lock 30 is often referred to as a cannula lock 30. It should be understood that the device that can be held by this cannula lock 30 are, in additional to needles and cannulae, other devices that are inserted subcutaneously in a patient to perform a medical diagnostic procedure and/or a medical treatment. Thus, a medical device that can be held fast by the cannula lock of this invention is an endoscope.

Cannula lock 30 includes a shell 36. Shell 36 is the assembly of the cannula lock 30 that is releasably secured to the section of the bone against which the cannula lock is placed. A brake 95 is moveably disposed in the shell 36. The brake 95 is the assembly of the cannula lock 30 that releasably receives the device the cannula lock 30 holds fixed relative to the bone against which the cannula lock is secured.

Figure 4:
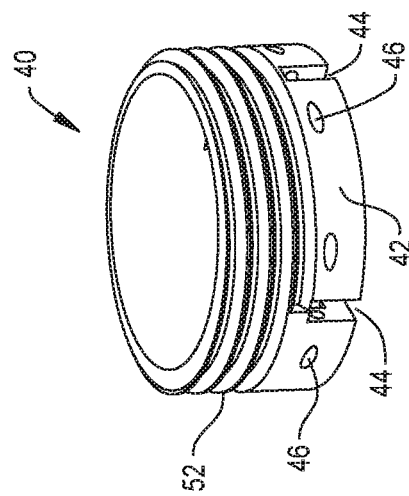
FIG. 4 is a perspective view of the base of the shell.
Figure 5:
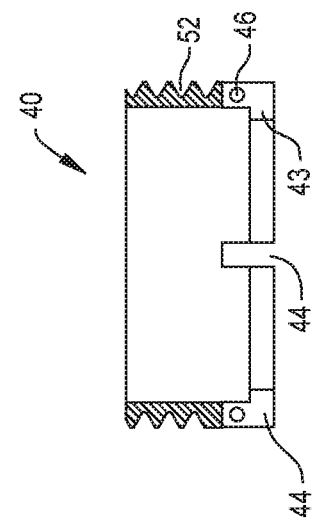
FIG. 5 is a cross sectional view of the base of FIG. 4.

The shell 36 includes a base 40 and a cap 70. The base 40, as seen best in FIGS. 4 and 5, is generally a ring shaped component. The base 40 has a distal section 42 the outer surface of which is in the form of a smooth cylinder. (Here, "distal" is understood to mean away from the practitioner performing the procedure using the lock 30 and towards the site on or in the patient to which the device 32 is directed. "Proximal" is understood to mean towards the practitioner and away from the site to which the device 32 is directed.) The outer diameter of distal section 42 is dimensioned to closely slip fit in a bore formed in the section of the bone against which the cannula lock 30 is to be secured. In versions of the invention in which the cannula lock 30 is used to hold a biopsy needle in place, the bore in the bone skull is typically less than 2.5 cm in diameter and can be 1.5 cm in diameter or less. Base 40 is also formed to have a lip 43 that extends radially inwardly from the distal end of distal section 42.

The shell base 40 is further formed to have a proximal section 52 that is contiguous with and located proximal to the distal section 42. Base 40 is formed so threading, (not identified), extends circumferentially around the outer surface of the shell proximal section 52.

Shell base 40 is further formed to have plural notches 44 that extend proximally upwardly from the distal end of the base. Each notch 44 extends partially through the base distal section 42. The notches 44 are equiangularly spaced apart from each other. Plural bores 46 are also formed in the distal section 42 of the shell base 40. The shell base 40 is formed so the longitudinal axes of the bores 46 are perpendicular to the proximal-to-distal longitudinal axis through the shell base 42. Each bore 46 is associated with a separate one of the notches 44. More particularly, the shell base 40 is formed so that each bore 46 intersects a separate one of the shell notches 44 near the top of the notch.

Cap 70 of the shell 36, as best seen in FIGS. 6, 7 and 8, includes a disk shaped head 72. A rim 74 extends downwardly from and circumferentially around the head 72. The inner cylindrical surface of the rim 74 is formed with threading, (threading not identified). The components forming shell 36 are arranged so the threaded rim 74 of cap 70 can engage the threading around proximal section 52 of the base 40.

The cap 70 is further formed to have a ring 76 that extends distally forward from the distally directed face of the head 72. Ring 76 is located radially inwardly of the rim 74. More particularly, the components forming shell 36 are arranged so that, when cap 70 is threaded over base 40, ring 76 is located slightly inwardly of inner surface of the proximal section 52 of the base. More, specifically, ring 76 is dimensioned so that when the cap 70 is threaded over the base 40, the ring is able to move freely along the inner surface of the base proximal section 52.

Cap 70 is also shaped so that the ring 76 and the portion of the head 72 located within the ring define a surface 78 that is a slice surface of a sphere. At the proximal end of the surface 78, the surface leads to an opening 80 that extends through the cap head 72. Surface 78 extends circumferentially around the proximal-to-distal longitudinal axis through the cap 70 and opening 80 is centered on this axis.

Cap 70 is further formed to have four wings 84 that extend radially outwardly from the rim 74. Wings 84 are equiangularly spaced apart from each other. The cap 70 is further formed so that each wing 84 is centered on a plane that intersects the longitudinal axis through the cap 70. Wings 84 serve as finger holds to facilitate the rotation of the cap 70 relative to the base 40

Figure 9:
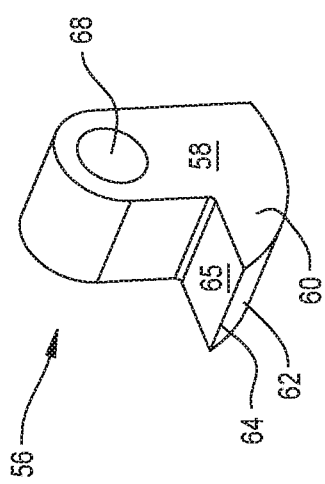
FIG. 9 is a perspective view of an anchor.

An anchor 56, one seen in FIG. 9, is moveably mounted in each of the notches 44 internal to the shell base 40. Each anchor 56 is shaped to have an elongated leg 58. Leg 58 is the portion of the anchor 56 that generally extends parallel to the longitudinal axis of the base 40. The top surface of the anchor 56 is curved to facilitate the pivoting of the anchor in the notch 44 in which the anchor is seated. A foot 60 extends outwardly from the distal end of the anchor. The bottom surface 62 of the anchor 56, the surface of the anchor that forms the sole of the foot 60 is curved. More particularly, surface 62 is curved so, as the surface extends outwardly, the surface curves upwardly. This surface extends to a planar surface 65 of the foot. Anchor 56 thus has an edge 64 where surfaces 62 and 65 meet.

Each anchor 56 is further formed with a through bore 68. The through bore 68 extends side to side through the anchor below the curved top surface of the leg 58.

Each anchor 56 is pivotally mounted in the notch 44 in which the anchor is seated. A pin 69, two pins identified in FIG. 2, is seated in the bore 46 associated with each notch 44. The portion of the pin 69 that extends through the notch 44 extends through the anchor bore 68 disposed in the slot. Pins 69 thus pivotally hold the anchors 56 to the shell base 40. Owing to the dimensioning of the components, when the inner surface of the anchors 56 are flush with the inner cylindrical surface of the base, the feet 60 of the anchors project outwardly from the outer surface of the base 40.

Figure 11:
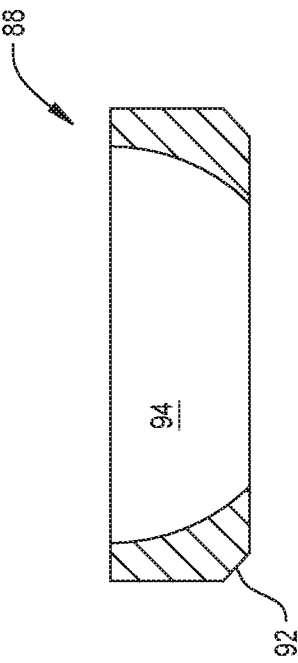
FIG. 11 is a cross sectional view of the drive ring of FIG. 10.
Figure 10:
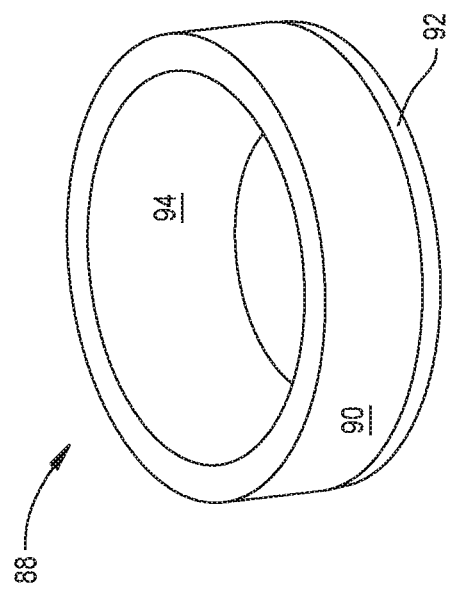
FIG. 10 is a perspective view of the drive ring.

A drive ring 88, now described by reference to FIGS. 10 and 11, is slidably disposed in the base 40 of shell 36. As implied by its name, the drive ring 88 is a ring-shaped structure. Drive ring 88 is formed so that, extending distally from the proximal end of the ring, there is an outer surface 90 that is cylindrical in shape. Surface 90 has a diameter that allows the drive ring 88 to closely slip fit against the inner surface of the shell base 40. Extending proximally-to-distally along the ring 88, surface 90 extends over at least 75% of the length of the ring. Extending distally from the distal end of surface 90, the drive ring has an inwardly tapered outer surface, surface 92. Thus, extending distally from the distal end of surface 90, the outer diameter of the drive ring 88 decreases.

Drive ring 88 is further formed to have an inner surface 94 that extends circumferentially around the inside of the ring. The drive ring 88 is formed so that surface 94 has a shape that is a slice section through a sphere. The center of the sphere around which inner surface 94 is centered is the point where a plane that extends along the proximal end of the drive ring and a proximal-to-distal longitudinal axis through the drive ring intersect. The void defined by surface 94 extends to a distal end opening of the drive ring 88, (opening not identified).

When the cap 70 is disposed against the drive ring 88, sliced spherical sections of cap surface 78 and drive ring surface 94 are centered on a common point.

Figure 13:
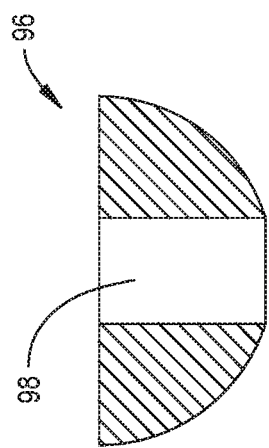
FIG. 13 is a cross sectional view of the bottom hemisphere of the brake.
Figure 12:
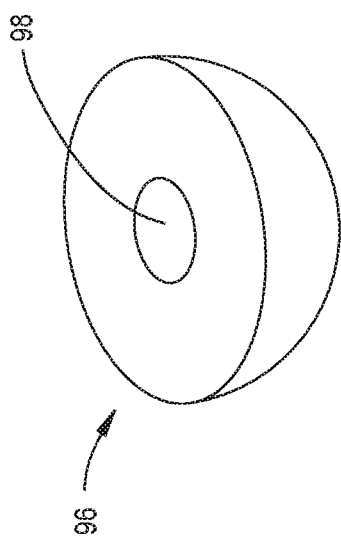
FIG. 12 is a perspective view of the base component, the bottom hemisphere of the brake.

Brake 95 includes plural components. One of these components is the base, now referred to as the bottom hemisphere 96 and now described by reference to FIGS. 12 and 13. Bottom hemisphere 96 is semi-spherical in shape. The bottom hemisphere 96 has a radius such that the hemisphere can seat in the void defined by inner surface 94 of drive ring 88. The components forming the cannula lock 30 are further shaped so that when the bottom hemisphere 96 is seated in the drive ring 88, the hemisphere can seat so the planar face of hemisphere is essentially coplanar with the planar proximal end face of the drive ring.

The bottom hemisphere 96 is formed to have a bore 98. Bore 98 extends longitudinally through the bottom hemisphere 96 from the planar face of the hemisphere. Bore 98 is centered on the longitudinal axis that extends proximally from the distal end pole of the hemisphere 96.

Figure 15:
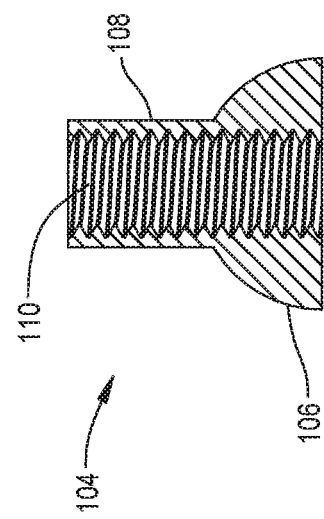
FIG. 15 is a cross sectional view of the top hemisphere of FIG. 14.
Figure 14:
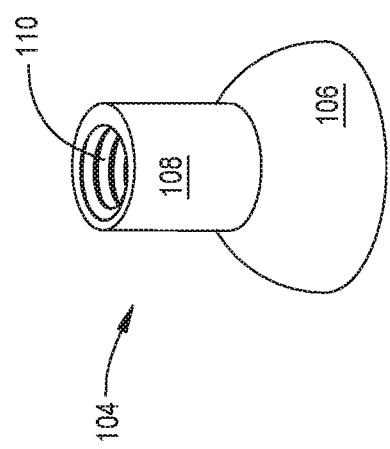
FIG. 14 is a perspective view of the head component, the top hemisphere, of the brake.

A second component of brake 95 is the head, now referred to as the top hemisphere 104. The top hemisphere 104, as seen best in FIGS. 14 and 15, includes a semispherical base 106. Base 106 has the same radius of curvature as the bottom hemisphere 96. A cylindrical stem 108, also part of the top hemisphere 104, extends upwardly from the base 106. Stem 108 is centered on the pole, the point of the curved portion of the base 106 spaced furthest from the planar face of the base.

Top hemisphere 104 is further formed to have a bore 110. Bore 110 extends along the proximal-to-distal longitudinal axis of the stem 108 as well as the portion of the base 106 located below the stem. The top hemisphere is formed so that bore 110 is threaded, (threading not identified).

Figure 16:
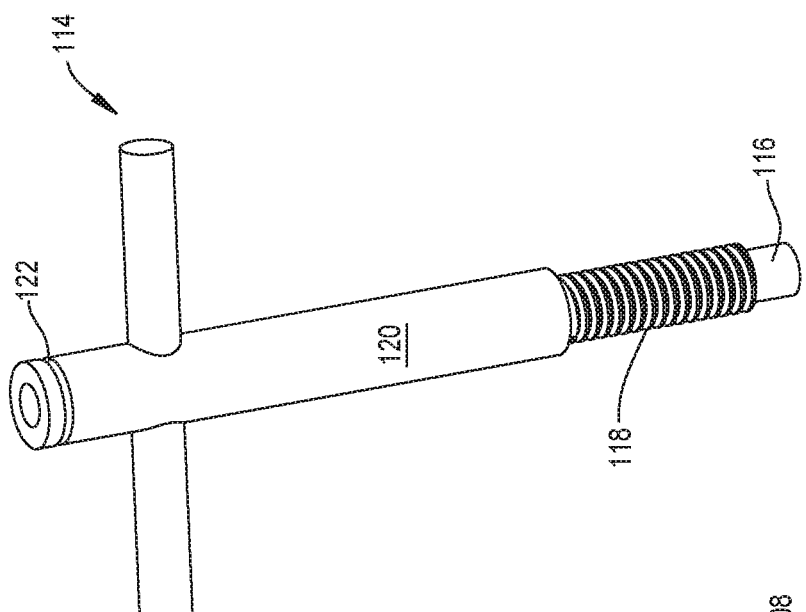
FIG. 16 is a perspective view of the access tube of the cannula lock.

The brake 95 includes a tube 114, best seen in FIGS. 2, 3 and 16. Tube 114 includes plural sections, each of which generally has a cylindrical outer surface. At the most distal end, the tube 114 includes a foot 116. Foot 116 is dimensioned to closely slip fit in and rotate in the bore 98 internal to the bottom hemisphere 96. Immediately adjacent and proximal to the foot 116, tube 114 is formed with a leg 118. The outer diameter of the leg 118 is greater than the outer diameter of the foot 116. More particularly, the outer diameter of the leg is such that the leg cannot seat in bore 98 internal to the bottom hemisphere 96. The outer diameter of leg 118 is formed with threading, (threading not identified). Tube 114 is formed so the threading of the leg 118 can engage the threading internal to bore 110 internal to the top hemisphere 104.

A trunk 120, located immediately proximal to leg 118, is the most proximal portion of tube 114. Trunk 120 has a smooth walled outer surface. The outer surface of trunk 120 is located radially outwardly of the threading of the foot 116. The tube 114 is formed so the trunk 120 subtends a length of at least 50% of the overall length of the tube. Tube 114 is formed so that a short distance, typically less than 0.5 cm from the proximal end of the tube, a groove 122 extends circumferentially around the trunk 120.

The tube 114 includes a longitudinally extending bore 124 that extends between the opposed proximal and distal ends of the tube. Tube 114 also is formed to have two diametrically opposed openings 126, one opening identified in each of FIGS. 1 and 2. Openings 126 are located in the trunk 120 at a position distal to groove 122. The openings 126 are coaxial and centered on an axis that is perpendicular to the longitudinal axis of the tube 114. Each opening 126 opens into the axially extending bore 124.

A rod 132 is used to set and release the cannula lock 30. Rod 132 is cylindrical in shape. Rod 132 is dimensioned to extend through the openings 126. Rod 132 is formed with a bore 134 that extends laterally through the rod. The rod 132 can be removably fitted in the openings 126 integral with the tube 114. The rod 132 is provided to facilitate rotation of the tube 114. When the rod 132 is fitted to the tube 114, the rod can be positioned so rod bore 134 is coaxial with the bore 124 internal to the tube 114. This allows the needle 32 or other device held in place by cannula lock 30 to be inserted through both the tube 114 and rod 132.

Figure 18:
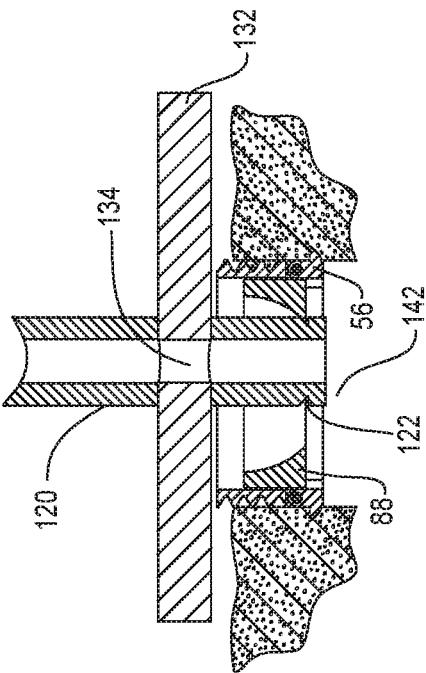
FIG. 18 is a cross sectional view of how the access tube functions as a tool to extract the drive ring.

To use cannula lock 30 to hold a device such as a needle 32 static, a bore is first drilled in the bone against which the lock is to be secured. FIGS. 3 and 18 illustrate such a bore, bore 142. Base 40 of the shell 36 is fitted in this bore 142. At this time, anchors 56 are able to freely pivot. When the base 40 is seated in the bore 142, the anchors 56 pivot inwardly, toward the longitudinal axis through the base 40. The anchors 56 are in a retracted state. The drive ring 88 is seated in the shell base 40. At this time, the tapered surface 92 of drive ring 88 seats against the inner surfaces of the legs 58 of the anchors 56. Bottom hemisphere 96 of the brake 95 is seated against inner surface 94 of the drive ring. Top hemisphere 104 of the brake 95 is seated over the bottom hemisphere 96 so the planar faces of the hemispheres abut and are in registration. As a result of this placement of the hemispheres 96 and 104, the bores 98 and 110 integral with, respectively the bottom hemisphere 96 and the top hemisphere 104 are aligned.

The tube 114 is fitted to the hemispheres 96 and 104. Specifically, the tube leg 118 is screwed into the top hemisphere bore 110 so the tube foot 116 projects into the bottom hemisphere bore 98.

The cap 70 of shell 36 is then fitted over the tube and screw secured to the complementary base 40. As a consequence of the cap 70 being screwed against the base 40, ring 76 integral with the cap abuts the outer circular face of the drive ring 88. The continued distal displacement of the cap 70 results in the like distal displacement of the drive ring 88. As a result of the distal displacement of the drive ring 88, first the tapered surface 92 then the main outer surface 90 of the drive ring 88 presses against the adjacent inner surfaces of the legs 58 of the anchors 56. This results in the radially outward displacement of the anchors 56. Specifically, the feet 60 of the anchors 56 pivot outwardly away from the outer surface of the base 40. As a consequence of the outward pivoting of the feet 60, the feet extend into the bone surrounding the bore 142 in which the base is seated. This embedding into the bone of feet 60 temporarily holds the base 40 as well as the components fitted to the base, to the bone.

The downward motion of drive ring 88 is stopped by the abutment of the distal end of the drive ring against lip 43 integral with the base 40.

Once the base 40 of the shell 36 is secured to the bone, the needle 32 or other device is inserted into the bore 124 internal to the tube. By manipulating tube 114 or the device extending out of the tube, hemispheres 96 and 104 are rotated in two axes about their common center point. The orientation of the brake 95 relative to the shell 36 is set to establish the trajectory of the device 32 as the device extends out of the bottom hemisphere and the base 40 of the shell 36 into the tissue.

Once the trajectory of the device 32 is set, the brake 95 is set. Brake 95 is set by rotating the tube 114. It is understood that, when the tube is so rotated, the bottom hemisphere 96 of the brake is in a static position. By extension the tube is likewise in a static position. Thus, owing to the threaded engagement of the top hemisphere 104 with the tube 114, the rotation of the tube translates the top hemisphere proximally, away from the bottom hemisphere 96. In other words, the head of the brake is displaced away from the base of the base of the brake. The movement of the top hemisphere presses base 106 of the hemisphere against the adjacent inner surface 78 of the cap 70. Thus, as a result of the movement of top hemisphere 104, the bottom hemisphere 96 is pressed against inner surface 94 of the drive ring 88 and the top hemisphere presses against the cap. Often, but not always, when the brake is set to the desired orientation, the hemispheres are oriented so the common axial line through bore 98 and 110 is not perpendicular to the horizontal plane along the top of the shell base 40. When brake 95 is so positioned, a fraction of the surface of the bottom hemisphere 96 is typically disposed against a portion of the cap inner surface 78 and a fraction of the surface of the top hemisphere base 104 is disposed against inner surface 94 of drive ring 88. When the components of the brake 95 are so engaged, the brake is set. The brake 95 does not move relative to the shell of the cannula lock 30.

As a result of brake 95 being set, the practitioner can continue to advance the device through the cannula lock 30 knowing that, since the brake will not move, the device 32 will advance along the designated path of travel. This facilitates the positioning of the distal end of the device at the intended target location for the device.

Once the procedure for which the device 32 is required is completed, the device is withdrawn from the tube 114. Tube 114 is rotated in the direction opposite the direction in which the tube is rotated to place the brake 95 in the set state. This rotation of the tube moves base 106 of the top hemisphere away from the position in which the base presses against the cap 70. The brake 95 is thus reset from the set to the initial released state. When the brake 95 is so released, it is a simple matter to unscrew the cap 70 from the base 40. Cap 70, top hemisphere 104, tube 114 and, finally, the bottom hemisphere 96 are withdrawn away from the rest of the components of the cannula lock 30.

Figure 17:
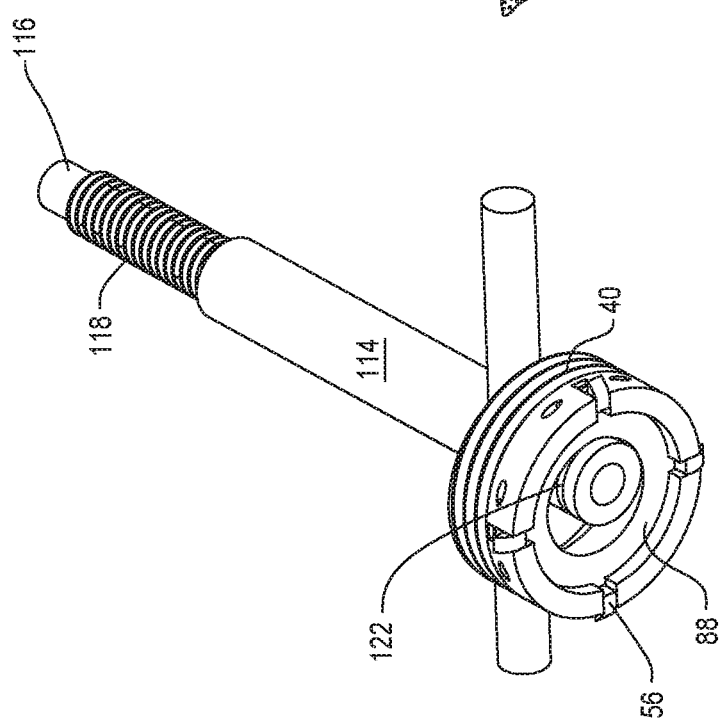
FIG. 17 is a perspective view of how the access tube functions as a tool to extract the drive ring.

At this time, the base 40 of shell 36 remains seated in the bone. Since surface 90 of drive ring 88 remains pressed against the anchors 56, the anchor feet 60 remained embedded in the bone. This can make it difficult to simply pull the base 40 out of bore 142. To facilitate the removal of the base 40, tube 114 is inverted. The tube 114 is positioned so the distal inner edge of the drive ring, as seen in FIGS. 17 and 18, is seated in the groove 122 formed in the tube 114. The tube 114 is used as a tool to extract the drive ring 88 from the base 40 of the shell 36.

Once the drive ring 88 is extracted from base 40, no component of the lock 30 impedes the inward pivoting of the anchors 56. With minimal manipulation of the base 40 the anchors will retract away of the bone in which the anchors are embedded. Once the anchors 56 is in this state, it is a simple task to withdraw the base 40 from the bore 142 in which the base is seated.

Cannula lock 30 of this invention is constructed so that the component of the brake 95 that sets and releases the brake, tube 114, moves with positioning of the brake. This means that, independent of the orientation of the brake 95, the component that sets the state of the brake is readily accessible. There is no concern that if the brake is placed in a particular orientation relative to the shell it will be difficult or impossible to set the brake. This means the brake can be set in essentially any orientation relative to the cannula when this lock is used to establish the trajectory of the device held in place by cannula lock 30.

Another benefit of this invention is gained by the fact that in most versions of the invention base 40 is cylindrical in shape. This means that bore 142, the bore in which the base is seated in bone likewise can be cylindrical in shape. This means that, to mount the cannula lock of this invention to bone, one does not have to engage in the more complicated process of first forming a bore in the bone that has a diameter that varies along the length of the bore.

It is likewise a further feature of cannula lock 150 that once the orientation of the tube 114 is set, the tube is locked in place, the brake 95 is set, by the rotation of the tube. Thus a single handle is all that is needed to set the tube 114 in a desired orientation and, once that orientation is set, lock the tube in that orientation.

A further feature of cannula lock 30 is that, as a consequence of the cap 70 being secured to the base 40, the anchors 56 secure the shell 36 to the bone in which the lock is seated. This eliminates the need to use other means to temporarily hold the cannula lock to the patient. Further, when it is time to remove the lock, minimal effort is required to withdraw the drive ring 88 so as to allow the movement of the anchors 56 so as to release the anchors from their locked state.

II. Second Embodiment

Figures 19, 20:
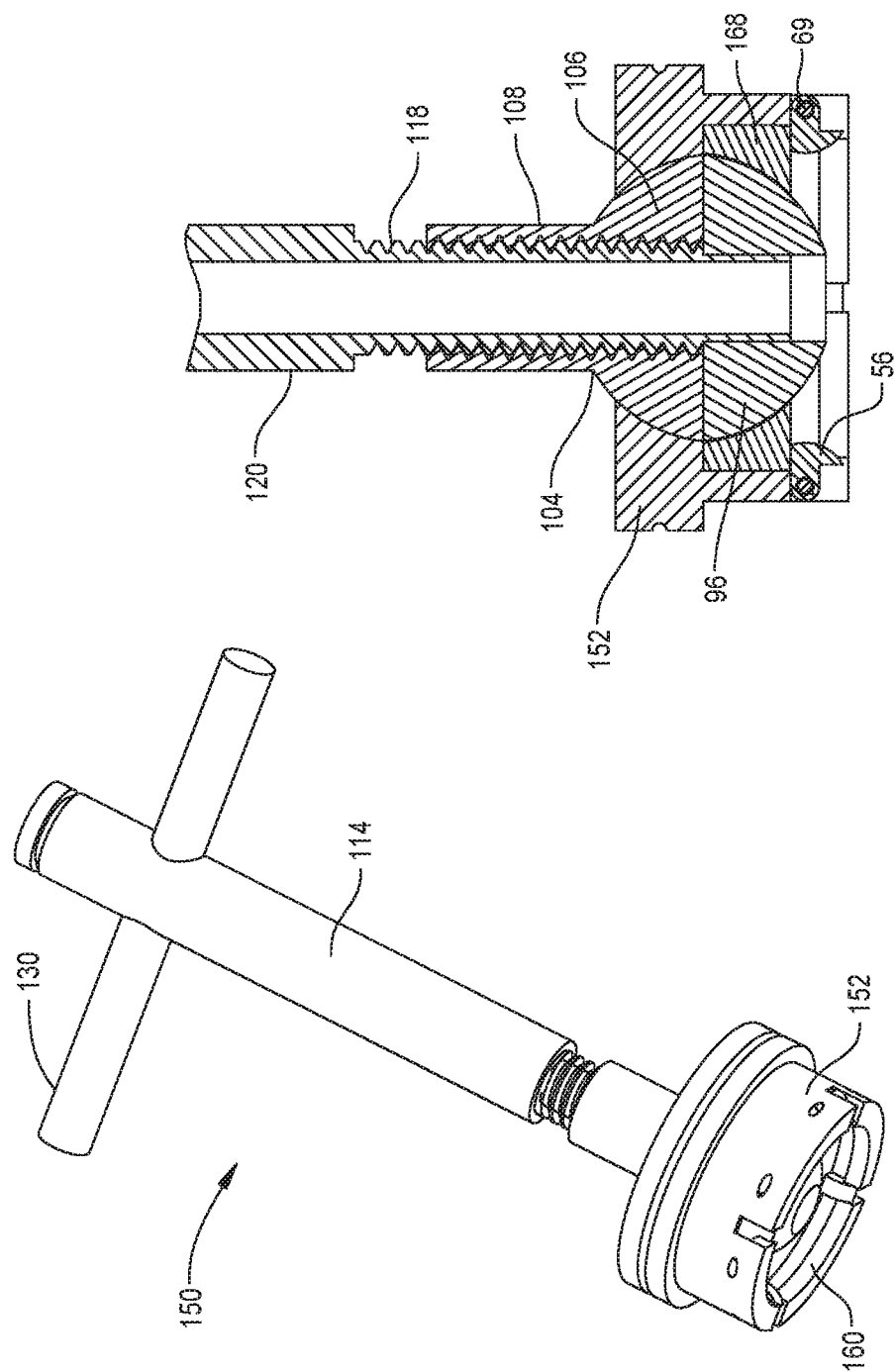
FIG. 19 is a perspective view of a first alternative cannula lock of this invention when the brake is in release state.
FIG. 20 is a cross sectional view of the alternative cannula lock when the brake is in the release state.

FIGS. 19 and 20 illustrate the basic features of a first alternative cannula lock 150 of this invention. Cannula lock 150 includes a shell 152. A drive ring 168 is slidably disposed in the shell 152. Also disposed in the shell 152 are a base 153 and a head 167. Base 153 is similar to the previously described bottom hemisphere 96. A difference between the two components is that the curved portion of base 153 subtends an arc of less than 180°. The planar face of base 153 has a diameter that is less than the diameter of the sphere defined by base 153.

Head 167 is similar to the previously described top hemisphere 104. A difference between the two components is that the distal portion 169 of the head 167 subtends an angle less than 180°. The distal planar face of head 167 has a diameter that is less than the diameter of the sphere defined the distal portion of the head. Head 167 includes the previously described stem 108 and bore 110. Tube 114 is threaded to and extends proximally away from head 167.

As seen in FIGS. 21 and 22, shell 152 of this version of the invention is a single piece structure. Shell 152 is formed to have a cylindrical hollow base 154 dimensioned to closely fit in the bore 142 into which the cannula lock 150 is to be seated. A cap 156 integral with the base 154 extends over the open proximal end of the base. In the illustrated version of the invention, the outer perimeter of cap 156 is located radially outwardly of the base 154. This limits the extent to which the shell 152 can be seated in the bore. The outwardly extending portion of cap 156 also serves as a finger hold to facilitate insertion and removal of the shell 152.

Shell 152 is further formed so as to have a lip 160 that extends radially inward from the inner surface of the base 154. Lip 160 extends circumferentially around the inside of the base adjacent the proximal end of the base.

The shell base 154 is formed to have the notches 44 and bores 46 integral with the base 40 of the first described cannula lock. In this version of the invention it is understood that notch 44 intersect and interrupt the lip 160. Anchors 56 are pivotally secured in the notches with the previously described pins 69. (The anchors are seen in FIGS. 20, 23 and 24. One pin 69 identified in FIGS. 20 and 24.)

Cap 156 of shell 152 is formed to have an inner surface 164 that is substantially identical in shape to surface 78 of cap 70. The most proximal end of surface 164 thus defines an opening 166 in the center of the cap 164.

Cannula lock 150 includes a drive ring 168. Drive ring 168 is similar in shape to drive ring 88. One difference between the drive rings is that the outer circumferential surface of drive ring 168 does not have, at the distal end of the ring, a taper. Thus, the outer circumferential surface of drive ring 168 is, along the length of the ring, cylindrical in shape. Drive ring 168 is formed with an inner surface (not identified) that is substantially identical in shape to surface 94 of drive ring 88. The components forming cannula lock 150 are dimensioned so that the drive ring 168 can move longitudinally within the cylindrical space internal to the shell 152. Thus the proximal-to-distal height of drive ring 168 is less than the proximal-to-distal length of the void space internal to the shell base 154 above the lip 160.

It should be understood that to assemble cannula lock 150, the lip 160 of the shell is often initially fabricated separate from the rest of the shell. Head 167, base 153 and drive ring 168 are initially fitted in the shell 152. Once these components are fitted in place, the lip 160 is secured to the shell. Lip 160 holds the base 153, head 167 and the drive ring 168 in the shell 152. Since lip 160 is intersected by notches 44, the lip may actually consist of plural arcuately shaped components that are fitted in place. Once lip 160 is in place, anchors 56 are pivotally secured to the shell 152.

Cannula lock 150 is readied for use by rotating tube 114 so that, as seen in FIG. 20, base 153 abuts the head 167. The brake is in the release state. When the cannula lock 150 is in this state, drive ring 168 is able to move within the shell 152. As a result of the spacing of the drive ring 168 away from the lip 160, the anchors 56 can in the retracted state. This allows base 154 of the shell 152 to be seated in the bore 142 (FIG. 18) formed to receive the lock 150. When appropriate, the device 32 is inserted in the tube 114.

The practitioner secures the cannula lock 150 in the bore 142 in which the lock is seated by rotating tube 114. Specifically, the tube 114 is rotated so as to cause the base 153 and head 167 of the brake to move apart from each other. When base 153 and head 167 move apart from each other, the distal movement of the base results in a like movement of the drive ring 168. As the drive ring 168 moves distally, the drive ring abuts and displaces the anchors 56. This displacement of the anchors results in the outward pivoting of the anchors from the retracted state to, as seen in FIGS. 23 and 24, the extended state. As seen best in FIG. 24 when the base and head 167 are so positioned, these components essentially define a common sphere.

The practitioner then uses the method described with respect to the first version of the invention to set the trajectory of the device 32 that is to be positioned by the cannula lock 150. Specifically, the tube 114 is pivoted to set the trajectory of the device 32.

Once the trajectory is set, the practitioner rotates the tube 114 to move the brake from the release state to the set state. Specifically, the tube 114 is rotated so as to attempt to further move the base 153 and head 167 of the brake further apart from each other. The blocking of the movement of the drive ring 168 results in a like blocking of the same distal movement of the base 153. The simultaneous proximal movement of distal section of the head 167 results in the base 153 and head distal portion 169 simultaneously presses against, respectively, the drive ring 168 and surface 164 of shell 152. The pressing of these brake components press against the shell 152 and the drive ring 168 places the brake in the set state.

Cannula lock 150 is thus designed so that, by the rotation of the tube 114, the device employed to actuate the brake, the practitioner is able to sequentially: move the anchors 56 from the retracted state to the extended state; and then set the brake. This sequential setting of the anchors 56 and the brake with a single control member simplifies the effort associated with securing the lock 150 in the tissue against which the lock is seated and setting the trajectory of the device 32 held by the lock.

III. Third Embodiment

Figure 26:
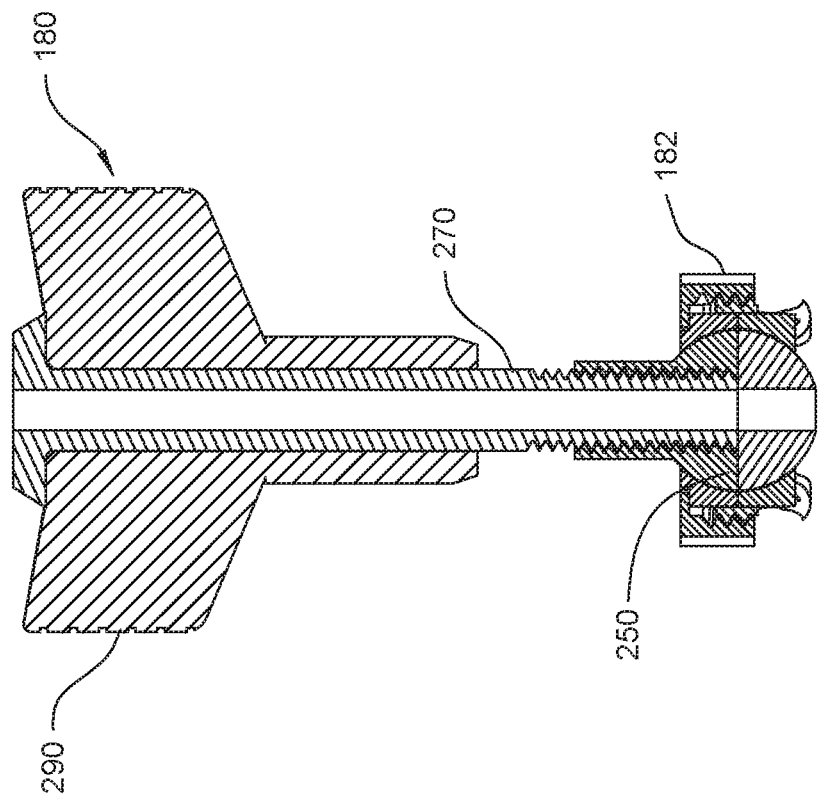
FIG. 26 is a cross sectional view of the cannula lock of FIG. 25.
Figure 25:
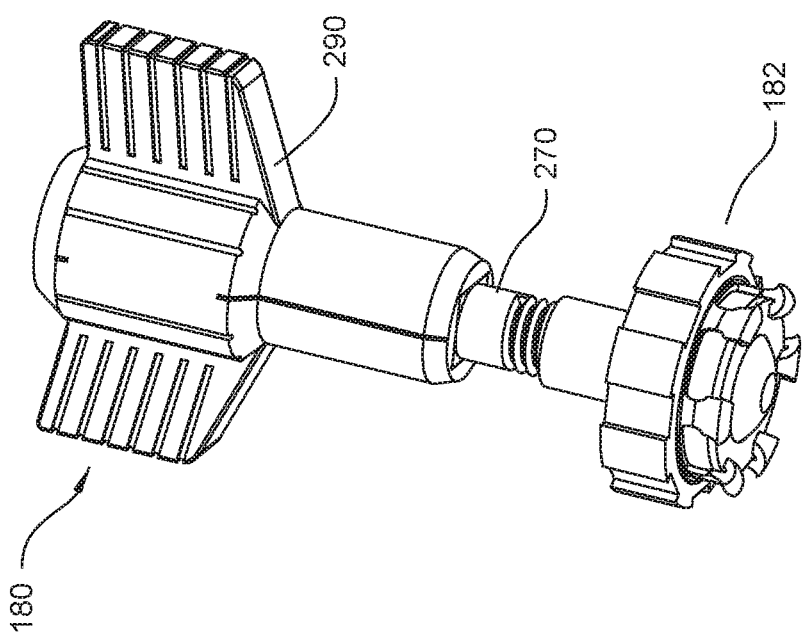
FIG. 25 is a perspective view of a second alternative cannula lock of this invention.

A third alternative cannula lock 180 of this invention is now described by initial reference to FIGS. 25-27. Cannula lock 180 includes a shell 182 in which a brake 250 is pivotally mounted. Brake 250 includes a proximally extending tube 270. The tube 270 receives the needle 32 (FIG. 1) or other device the position of which is to be set and locked relative to the tissue to which the cannula lock 180 is mounted.

Figure 29:
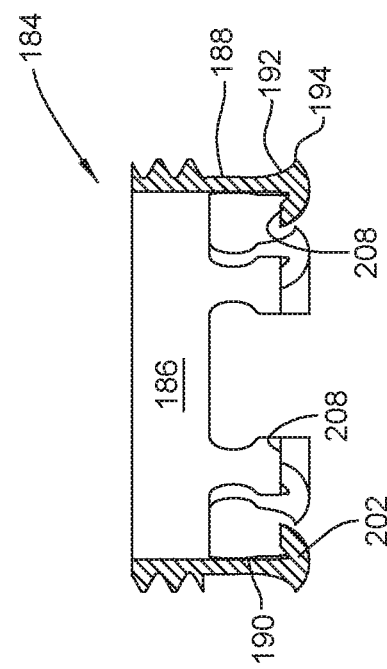
FIG. 29 is a cross sectional view of the base of FIG. 28.
Figure 28:
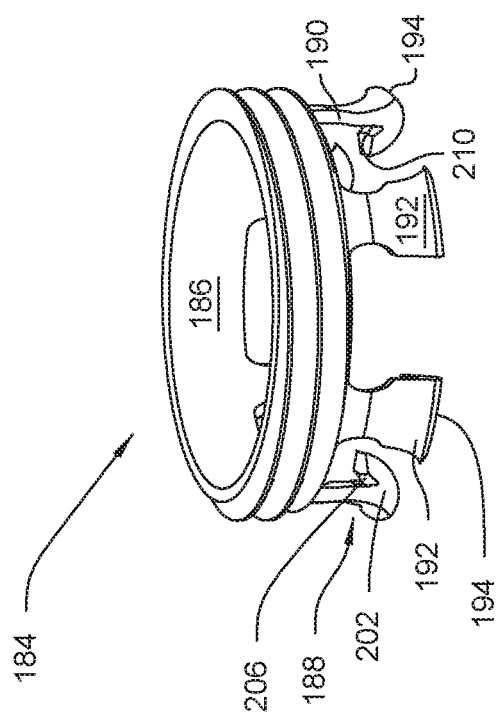
FIG. 28 is a perspective view of the base of the cannula lock of FIG. 25.

Shell 182 includes a base 184 and a cap 220. The base 184, as seen best in FIGS. 28 and 29, includes a cylindrically shaped rim 186. Base 184 is formed so that the outer surface of the rim is threaded, (threading not identified). The inner cylindrical inner wall of the rim 186 is smooth.

Figure 39:
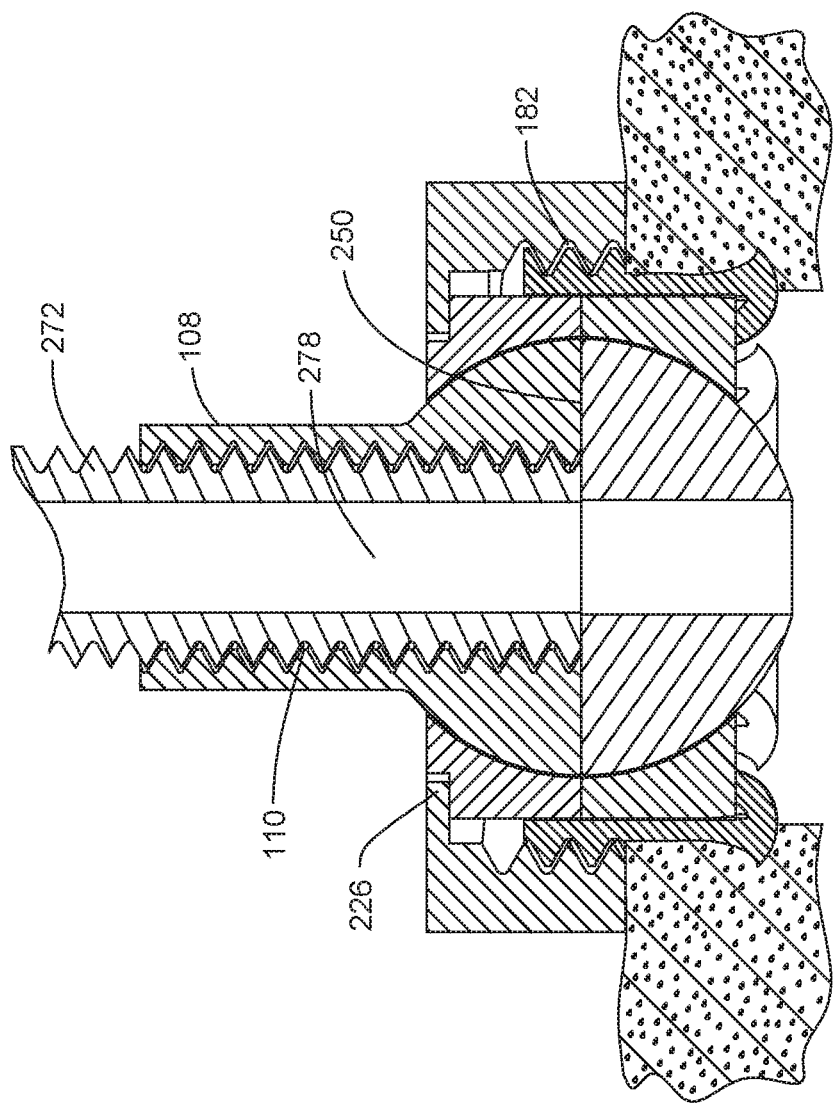
FIG. 39 is an enlarged cross sectional view of the distal end of the cannula lock of FIG. 25 embedded in tissue, specifically, bone.

Plural anchors 188, one anchor identified, extend distally downwardly from the distal end of the rim 186. Each anchor 188 includes a leg 190. The leg 190 is the part of the anchor that projects distally from the rim 186. At the distal end of each leg 190 a heel 192 extends outwardly, away from the proximal to distal longitudinal axis through the base 184. The heels 192 are formed so that the outermost portion of the heel is in the form of an edge 194. At the distal end of the each leg a foot 202 projects inwardly from the foot. Each foot 202 has a top surface 208. Feet top surfaces 208 are in a plane that is perpendicular to the longitudinal axes of the legs 190 when the anchors are in the undeployed state. Each foot 202 is formed so there is a small V-shaped gap 210 between the leg 190 of the anchor and the associated foot top surface 208. A recessed surface, surface 206 extends downwardly from the end of each top surface 208 adjacent a leg 190 so as to define one perimeter of the gap 210, (one surface 206 identified in each of FIGS. 29 and 39). The outer perimeter of each gap 210 is defined by a section of the inner surface of the associated leg 190.

Anchor legs 190, it is understood are both integral with rim 186 and able to pivot outwardly relative to the rim. In the illustrated version of the invention, base 184 is formed so that the arcuate length of each leg 190 it is shortest width, is less than the arcuate length of the heel 192 and foot 202 that is integral with and located distal to the leg. This narrow width of the anchor leg 190 contributes to the ability of the leg to flex, pivot, outwardly.

From FIGS. 30 and 31 it can be seen that the cap 220 of the shell 182 is a cylindrical nut like structure. Cap 220 it is understood is designed to fit over and threadedly engage the rim 186 of base 182. Not identified is the threading around the inner cylindrical surface of the cap 220 that engages with the threading around the outer surface of rim 186. Arcuately spaced apart ribs 224 extend radially outwardly from the outer cylindrical surface of cap 220. Ribs 224 and the gaps between the ribs facilitate the finger and thumb grasping for rotation of the cap 220.

Cap 220 is further formed so as to a lip 226 that extends radially inward from the inner surface of the cap. The cap 220 is formed so that lip 226 extends inwardly from the proximal end of the cap.

Figure 33:
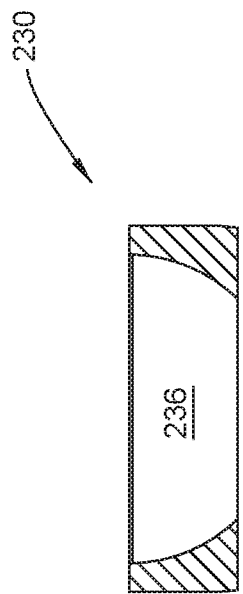
FIG. 33 is a cross sectional view of the distal drive ring of FIG. 25.
Figure 32:
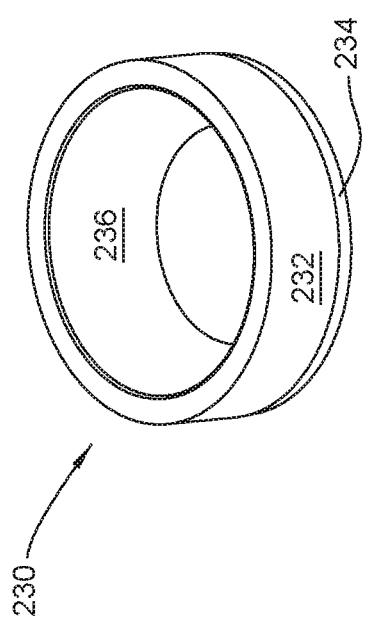
FIG. 32 is a perspective view of the distal drive ring of cannula lock of FIG. 25.

A distal drive ring 230, now described by reference to FIGS. 32 and 33, is slidably disposed in the base 184 of shell 182. Drive ring 230 is formed so that, extending distally from the proximal end of the ring, there is an outer surface 232 that is cylindrical in shape. Surface 232 has a diameter that allows the drive ring 230 to closely slip fit against the inner surfaces of the rim 186 and legs 190 of the base 184. Surface 232 does not extend the complete Extending proximal-to-distal length along the ring 230. Extending distally from the distal end of surface 232, distal drive ring 230 has an inwardly tapered outer surface, surface 234. Thus, extending distally from the distal end of surface 90, the outer diameter of the distal drive ring 230 decreases.

The distal drive ring 230 is further formed to have an inner surface 236 that extends circumferentially around the inside of the ring. Surface 236 can be considered similar if not identical to surface 94 of drive ring 88.

Figure 35:
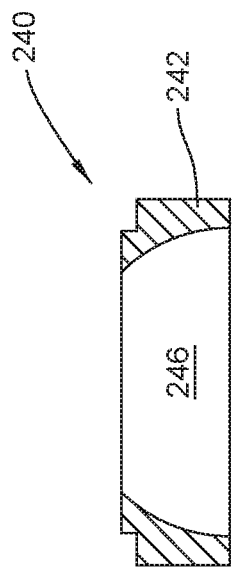
FIG. 35 is a cross sectional view of the proximal drive ring of FIG. 34.
Figure 34:
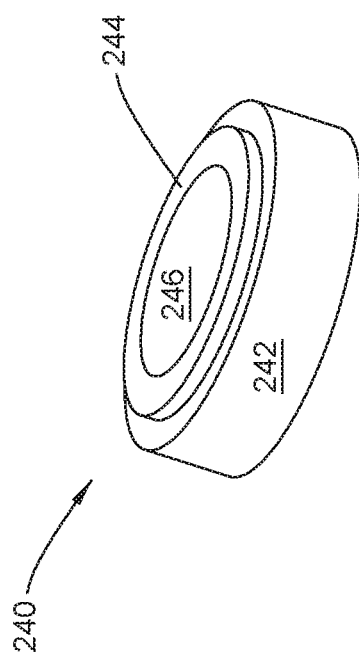
FIG. 34 is a perspective view of the proximal drive ring of the cannula lock of FIG. 25.

Also disposed in the shell 182 is a proximal drive ring 240 seen best in FIGS. 34 and 35. Drive ring 240 has a core 242. Core 242 has a cylindrical outer wall, (not identified) with a diameter equal to the diameter of surface 232 of the distal drive ring 230. The proximal drive ring also has a head 244 that projects proximally away from the proximal end of the core. Head 244 has a diameter less than that of core 242. More particularly, the head has a diameter that is typically at least 1 mm less than the inner diameter of the lip 226 integral with cap 220.

The proximal drive ring 240 is further formed to have an inner surface 246 that extends circumferentially around the inside of the ring. The drive ring 240 is formed so that surface 246 has a shape that is a slice section through a sphere. More particularly surface 246 can be considered to in shape, mirror surface 236 of the distal drive ring. Surface 246 extends proximally from the distal end of core 242 to the proximal end of the head 244. Thus, head 244 of the proximal drive ring 240 appears ring like in shape.

Brake 250 includes the bottom hemisphere 96 and top hemisphere 104 of brake 95.

The tube 270 of cannula lock 180 is seen best in FIGS. 36 and 37. Tube 270 is formed to have a stem 272 that is the distal portion of the tube. The outer surface of stem 272 is formed with threading, (not identified). The tube 270 is formed so that stem 272 can seat in bore 110 of the top hemisphere 104 and engage the threading in bore 110. Proximal to stem 272, tube 270 is formed to have an elongated trunk 274. Not identified is the undercut between the stem 272 and trunk 274. In the illustrated version of the invention, the tube 270 is shaped so that in planes perpendicular to the proximal to distal longitudinal axis through the tube the torso is square in shape. The tube is formed so that the outer perimeter of the trunk 274 is located radially outwardly of the stem 272.

A head 276 forms the proximal end section of the tube 270. The head 276 extends radially outwardly from the trunk 274. In the illustrated version of the invention, The outer perimeter of the head 276 is circular in shape. A bore 278 extends longitudinally through tube 270. Bore 278 thus extends distally, from and through the head 276, through the trunk 274 and through the stem 272 to the distal end of the stem. Bore 278, like bore 124, is dimensioned to receive the medical device the cannula lock is used to hold in a fixed position.

A finger grip 290, now described by reference to FIG. 38, is disposed over the trunk 274 of tube 270. The Finger grip 290 is formed to have a cylindrical collar 292. A head 294 is formed integrally with and located proximally forward of the collar 292. The finger grip 290 is formed so a bore 296 extends proximally to distally axially through the head 294 and collar 292. Bore 296 is dimensioned to tightly receive trunk 274 of the tube 270. Thus, in the illustrated version of the invention, bore 296 has a square cross sectional shape to match the cross sectional shape of the trunk 274.

Finger grip 290 includes two ears 302 that extend radially outwardly from the head 294. The finger grip 290 is formed so the ears are, relative to the proximal to distal longitudinal axis of the collar diametrically opposed to each other. Ears 302 function as the thumb and finger holds of the tube 270 as to facilitate the manual rotation of the tube.

Cannula lock 180 is assembled by first placing the distal drive ring 230 in the base 184. The movement of the distal drive ring out of the base is stopped by the abutment of the distal end of the ring against the top surfaces 208 of feet 202. Bottom hemisphere 96 is seated against the curved inner surface 236 of the distal drive ring. The top hemisphere 104 is placed against the bottom hemisphere 96 so that the planar surfaces of the hemispheres abut.

Proximal drive ring 240 is seated over the top hemisphere 104 so stem 108 projects out of the proximal end of the drive ring 240. Cap 240 is then at least partially screw secured to the base 184. As a result of the cap 240 being fitted to the base 184, lip 226 seats in the space around head 244 of the proximal drive ring 240. Assembly of cannula lock 180 is completed by the threading of stem 272 of tube 270 into threaded bore 110 of the top hemisphere 104.

To lock a medical device to a patient using cannula lock 180 the previously described bore 142 is formed in the bone. Since base 184 is generally cylindrical, bore 142 can be cylindrical in shape. Bore 142 should have a diameter that facilitates the close slip fitting of the anchors 188, specifically the heels 192 of the anchor, in the bore.

Lock 180 is locked to the tissue by the rotation of cap 220. Specifically, the cap 220 is rotated to move distally. The distal movement of the cap results in the like distal displacement of the proximal drive ring 240. This movement of the proximal drive ring 240 results in the like distal movement of the distal drive ring 230. Distal drive ring 230, in turn, presses against top surfaces 208 of feet 202. Owing to the flexible nature of the legs 190, the anchors in response to this force, pivot outwardly. More specifically heels 190 embed into the bone forming the perimeter of bore 142. This embedded process is facilitated by the fact that edges 194 of the heels 192 slice into the bone. The embedding of the anchors in the bones serve to secure the cannula lock 180 in the bore 142.

As a result of the outwardly flexure of the anchors 188, the feet 202 likewise pivot outwardly. This can result in surfaces 206 of the anchors pivoting into a position in which these surfaces are lie in close to or in a planes that is perpendicular to the longitudinal axis through the base. These surfaces 210 thus function as stops that prevent further distal movement of the distal drive ring.

Once cannula lock 180 is so secured, the orientation of the brake 250 and tube 270 are set relative to shell 182. The same processes used to set the orientation of brake 95 and tube 114 are used to set the orientation of the brake 250 and tube 270.

Once the orientation of the brake and tube are set, the brake is set so as to be locked in that orientation. This process is performed by rotation the tube 270. Finger grip 290 serves as the thumb and finger hold to facilitate the rotation of the tube 270. Since the anchors 188 are embedded in bone, the anchors cannot move. Given that the anchors 188 are static, the anchors hold the distal drive ring 230 static. Consequently, the bottom hemisphere 96 is likewise held static. By extension tube 270 is likewise in a static position. Thus, owing to the threaded engagement of the top hemisphere 104 with the tube 270, the rotation of the tube translates the top hemisphere proximally, away from the bottom hemisphere 96. The movement of the top hemisphere presses base 106 of the hemisphere against the adjacent inner surface 246 of the proximal drive ring 240. The proximal drive ring 240 is restricted from proximal movement by the abutment of the ring against lip 226 integral with cap 20. When the components of the brake 250 are so engaged, the brake is set. The brake 250 does not move relative to the shell 182 of the cannula lock 150.

It should be understood that cannula lock 180, like cannula lock 30, is constructed so that the resetting of the brake 250 from the set state to the release state does not affect the deployment of the anchors 188. This means that after the orientation of brake 250 and tube 270 are set and locked, the orientation of these components can be reset and then relocked into place without a concern that such activity could result in the anchors being released from their deployed state. If the anchors are so released, there is a possibility that the position of the shell relative to the bone would shift. If this shifting is allowed to occur, it could complicate the process of setting the tube 270 so it has the desired orientation. Again though, since the anchors 188 remain deployed if the brake 250 is released, the possibility of such shifting as a result of the reorienting of tube 270 is substantially eliminated.

Further, as with cannula lock 30, one can, with a single hand, first set the orientation of tube 270 and then, by rotating the tube, set the brake so as to lock the tube in a desired orientation. There is no need to, with a first hand, hold the tube steady while using a second hand to set the brake.

IV. Alternative Embodiments

It should be understood that the foregoing is directed to specific embodiments of the invention. Other versions of the invention may have features different from what has been described. The features of the disclosed versions of the invention may also be combined.

For example, some cannula locks of this invention may include the shell with anchors 56 and not include the brake assembly. In these versions of the invention, internal to the shell may be a conventional clamp that holds the device static relative to the shell.

Alternatively, a cannula lock of this invention may include the described brake 95 or 250 or a variation of this brake but not the described anchors 56 that pivot into tissue to hold the shell fast.

A brake of this invention may have features different from what has been described. For example, there is no requirement that all brakes be constructed so the angular orientation of the bore through which the device extends can be set around two axis. In some versions of the invention it may be desirable to have a brake the orientation of which can be set around only a single axis. In these versions of the invention the base and head of the brake may each be formed out of a component that is semi-cylindrical in shape.

There is no requirement that, in all versions of the invention, the actuator that moves the base and head of the brake between the set and released states be the tube that defines the bore for receiving the device that is held in place by the lock. For example it may be desirable in some versions of the invention that the actuator may be one or more set screws. These screws, it is understood, move with at least the head of the brake. Alternatively, the actuator that sets and releases the brakes may include a lever that is static against one of the brake base or head and moves against the other of the brake head or base.

It should likewise be appreciated that a cannula lock of this invention may be constructed so that, when the brake is transitioned from the release state to the set state, the head remains relatively static and the base moves relative to the head.

Likewise, while the particular anchors are configured to move radially outwardly from the shell, they may not engage in these motions in all versions of the invention. In some versions of the invention, the anchors are configured to, upon deployment, move distally relative to the shell. Likewise the structure of the anchors should of course be expected to vary based on the type of tissue into which the anchors are intended to extend. So if the cannula lock is intended for placement against soft tissue, the anchors may be barb or needle shaped to facilitate the penetration of and releasable locking of the anchors into the soft tissue. It should thus also be appreciated that while in the described version of the invention, the anchors when in the retracted state do not extend beyond the adjacent outer surface of the shell base 40 this need not be the construction of all versions of the invention. In some versions of the invention, even when the anchors are retracted, portions of the anchors may extend outwardly from the adjacent outer surfaces of the shell.

The anchors may have different shapes than described. Thus, there is no requirement that in all versions of the invention that anchors that also function as stops to prevent the distal movement of the driver be formed with surfaces similar to the above described surfaces 206. Alternatively, when a stop surface is present, this surface may not always be planar in shape. Likewise in order to provide anchors that pivot, it may not be necessary to so design the anchors to have pivoting sections that are shorter in arcuate length than the more distal sections of the anchor that embed in tissue. It is within the scope of this invention that anchor include a proximal section that is formed from a flexible material and a distal section formed from a more rigid material. It should thus be appreciated that the proximal section of the anchor is therefore able to flex, while the distal section is able to embed into tissue.

In some versions of the invention, the anchor may be a layer of adhesive that holds the shell to the tissue through which the device is to be inserted. An adhesive is often used as an anchor in versions of the cannula that are secured to a section of skin. From the foregoing it should likewise be understood that some cannula locks of this invention may only have a single anchor.

Also while not shown, it should be appreciated that the cannula lock of this invention may also include a supplemental lock. The supplemental lock holds the device 32 held in place by the brake 95 static relative to the brake. This supplemental lock may be as simple as an elastomeric sleeve that friction holds the device to the brake. This supplemental lock may be a multi-component assembly such as a set of collet feet that are compressed over the device by a sleeve. Typically, but not always this supplemental lock is fitted to the tube 114.

The features of the described versions of the invention may be interchanged. For example, either the first or second cannula locks 30 and 150 of this invention may include the base with integral anchors of cannula lock 180. Similarly a version of cannula lock 180 may include a base with internal distally located static steps. These steps would extend inwardly from the inner wall of the base. These steps would function as the structural members that, after the driver deploys the anchors, prevents further distal movement of the driver.

It is likewise within the scope of this invention to manufacture a version of cannula lock 150 wherein the anchors are integral with the shell so that the shell is formed out of two components. Specifically that shell could be formed out of a base and a cap. The base is the distally located component from which the anchors, anchors like anchors 188, extend. The cap is the proximal portion of the shell, the portion of the shell formed with the head piece from which the stem 108 of the top hemisphere extends. Once these components are separately manufactured they can be press fit together to form the single piece shell with integral anchors. A benefit is this type of assembly is that it may be cost effective to manufacture these components separately and fit them together than to manufacture a single component that includes all the features of a shell with integral anchors.

Further while the lock of this invention is primarily intended for medical use, an alternative lock of this invention may be constructed for alternative uses. For example, a lock of this invention may be mounted to a container or pipe through which a fluid is flowed in order to selectively position a probe in the container or pipe.

Accordingly, it is an object of the appended claims to cover all such variations and modifications that cover the true spirit and scope of this invention.

What is claimed is:

1. A cannula lock for performing a medical or surgical procedure with a device, said cannula lock including:
   a shell including at least one anchor attached to said shell for releasably holding said shell static to a section of tissue against which said shell is placed; and
   a brake defining a bore dimensioned to receive the device, said brake including a base and a head disposed in said shell and, configured to rotate around at least one axis within said shell so angular orientation of the device relative to said shell can be selectively set; and
   an actuator extending between said base and head so as to rotate with said base and said head and selectively move one of said base or said head away from the other of said head or said base to transition said brake from a release state in which said base and head are able to rotate within said shell and said angular orientation of the device can be set, and a set state in which said base and said head are spaced apart from each other and press against surfaces internal to said shell to hold the device in a fixed angular orientation relative to said shell.

2. The cannula lock of claim 1, wherein said base of said brake is formed with a portion of said bore and said head of said brake is formed with another portion of said bore, wherein said base and said head are configured so that the different portions of the bores are aligned in said release state.

3. The cannula lock of claim 2, wherein said brake further includes a tube that is seated in at least one of the bore portion of said base or the bore portion of said head, said tube being formed with another bore for receiving the device and being connected to at least one of said base or said head for moving one of said base or said head towards and away from the other of said head or said base so that said tube functions as said actuator of said brake.

4. The cannula lock of claim 3, wherein said base, said head and said tube of said brake are collectively configured so that said tube engages and is able to rotate relative to said base and said tube threadingly engages said head.

5. The cannula lock of claim 1, wherein said base, said head and said actuator of said brake are configured to rotate around two axes relative to said shell.

6. The cannula lock of claim 1, wherein:
   the shell includes a base to which the at least one anchor is attached and a cap, said base and cap being collectively arranged so said cap is removably attached to said base; and
   said base and head of said brake are disposed between said base and said cap of said shell.

7. The cannula lock of claim 6, wherein said cap is threadedly connected to said base of said shell.

8. The cannula lock of claim 1, wherein said at least one anchor is moveably attached to said shell and is configured to embed into the tissue against which said shell is placed.

9. The cannula lock of claim 1, wherein said at least one anchor is integrally formed with a portion of said shell and as able to flex relative to the portion of said shell with which the at least one anchor is integral.

10. The cannula lock of claim 1, wherein said at least one anchor is configured to embed into bone.

11. The cannula lock of claim 1, further comprising a drive member that is moveably mounted to said shell, and said drive member is configured to, upon movement, abut the at least one anchor so as to cause the at least one anchor to embed into tissue.

12. The cannula lock of claim 11, wherein:
   said shell includes a base to which the at least one anchor is attached and a cap, said base and said cap being collectively arranged so said cap is removably attached to said base;
   said drive member is positioned to abut against said cap of said shell so that the movement of said cap towards said base of said shell results in the displacement of said drive member that results in the movement of the at least one anchor; and
   said base and head of said brake are disposed between said base and said cap of said shell.

13. The cannula lock of claim 11, wherein:
   said drive member is disposed in said shell; and
   said brake is disposed in said shell so that, when said brake is move to the set state, at least one of said base or said head pushes against a surface of said drive member.

14. The cannula lock of claim 1, wherein the at least one anchor comprises a plurality of anchors which are mounted to said shell.

15. A cannula lock for performing a medical or surgical procedure with a device, said cannula lock including:
- a shell defining a void space and including a shell base, and at least one anchor pivotably coupled to the shell base and including a feature configured to engage a section of tissue against which said shell base is placed;
- a brake including a brake base and a head collectively disposed in said void space of said shell and configured to rotate around at least one axis within said void space so angular orientation of the device relative to said shell can be selectively set; and
- an actuator extending between said brake base and head and configured to selectively move one of said brake base or said head away from the other of said head or said brake base to press against surfaces internal to said shell at least partially defining said void space, thereby pivoting said at least one anchor outwardly from a retracted state within said shell base to an extended state beyond said shell base to engage the section of tissue.

16. The cannula lock of claim 15, further including a drive member movably disposed within said shell base and including one of said surfaces internal to said shell at least partially defining said void space, wherein said drive member is configured to be moved by said actuator to engage said at least one anchor to pivot said at least one anchor from said retracted state to said extended state.

17. The cannula lock of claim 16, wherein said shell further includes a cap threadably coupled to said shell base and including another one of said surfaces internal to said shell at least partially defining said void space with said cap configured to be moved to cause said drive member to engage said at least one anchor.

18. The cannula lock of claim 15, wherein said shell base defines a notch with said at least one anchor disposed within said notch in said retracted state.

19. The cannula lock of claim 15, wherein said at least one anchor is a flexible leg configured to resiliently pivot outwardly from said retracted state to said extended state.

20. The cannula lock of claim 15, wherein said head defines a bore including internal threads with said actuator including external threads configured to engage said internal threads of said head, wherein rotation of said actuator with said complementary threads engaged is configured to move one of said brake base or said head away from the other of said head or said brake base.

* * * * *